(12) United States Patent
Lee et al.

(10) Patent No.: US 9,260,470 B2
(45) Date of Patent: Feb. 16, 2016

(54) SIRNA STRUCTURE FOR MINIMIZING OFF-TARGET EFFECTS CAUSED BY ANTISENSE STRANDS, AND USE THEREOF

(75) Inventors: Dong Ki Lee, Seoul (KR); Dua Pooja, Gyeonggi-do (KR)

(73) Assignee: SUNGKYUNKWAN UNIVERSITY FOUNDATION FOR CORPORATE COLLABORATION, Gyeonggi-Do (KR)

( * ) Notice: Subject to any disclaimer, the term of this patent is extended or adjusted under 35 U.S.C. 154(b) by 0 days.

(21) Appl. No.: 13/505,965

(22) PCT Filed: Nov. 4, 2010

(86) PCT No.: PCT/KR2010/007771
§ 371 (c)(1),
(2), (4) Date: Sep. 17, 2012

(87) PCT Pub. No.: WO2011/056005
PCT Pub. Date: May 12, 2011

(65) Prior Publication Data
US 2013/0130377 A1    May 23, 2013

(30) Foreign Application Priority Data
Nov. 4, 2009    (KR) .......................... 10-2009-0105808

(51) Int. Cl.
*C07H 21/04* (2006.01)
*C07H 21/02* (2006.01)
*C12N 15/11* (2006.01)
*C12N 15/113* (2010.01)

(52) U.S. Cl.
CPC .............. *C07H 21/02* (2013.01); *C12N 15/111* (2013.01); *C12N 15/113* (2013.01); *C12N 2310/14* (2013.01); *C12N 2310/533* (2013.01); *C12N 2320/53* (2013.01)

(58) Field of Classification Search
None
See application file for complete search history.

(56) References Cited

U.S. PATENT DOCUMENTS

| | | | |
|---|---|---|---|
| 2005/0020521 A1 | 1/2005 | Rana | |
| 2005/0186586 A1* | 8/2005 | Zamore et al. | 435/6 |
| 2009/0208564 A1* | 8/2009 | Li et al. | 424/450 |

OTHER PUBLICATIONS

Doench, John G., et al., "siRNAs can function as miRNAs," Genes & Development, 2003, pp. 438-442, vol. 17.
Saxena, Sandeep, et al., "Small RNAs with Imperfect Match to Endogenous mRNA Repress Translation," The Journal of Biological Chemistry, 2003, pp. 44312-44319, vol. 278.
Ohrt, Thomas, et al., "Fluorescence correlation spectroscopy and fluorescence cross-correlation spectroscopy and fluorescence cross-correlation spectroscopy reveal the cytoplasmic origination of loaded nuclear RISC in vivo in human cells," Nucleic Acids Research, 2008, pp. 6439-6449, vol. 36.
Martin, Scott E. et al., "Mismatched siRNAs downregulate mRNAs as a function of target site location," FEBS Letters, 2006, pp. 3694-3698, vol. 580.
Jackson, Aimee L. et al., "Noise amidst the silence: off-target effects of siRNAs?" Trends in Genetics, 2004, pp. 521-524, vol. 20.
Chang, Chan II, et al., "Asymmetric Shorter-duplex siRNA Structures Trigger Efficient Gene Silencing With Reduced Nonspecific Effects," Molecular Therapy, 2009, pp. 725-732, vol. 17.
Elmen, Joacim, et al., "Locked nucleic acid (LNA) mediated improvements in siRNA stability and functionality," Nucleic Acids Research, 2005, pp. 439-447, vol. 33.
Sano, Masayuki et al., "Effect of asymmetric terminal structures of short RNA duplexes on the RNA interference activity and strand selection," Nucleic Acids Research, 2008, pp. 5812-5821, vol. 36.
Sun, Xiangao, et al., "Asymmetric RNA duplexes mediate RNA interference in mammalian cells," Nature Biotechnology, 2008, pp. 1379-1382, vol. 26.
Jackson, Aimee L. et al., "Expression profiling reveals off-target gene regulation by RNAi," Nature Biotechnology, 2003, pp. 635-638, vol. 21.
Jackson, Aimee L. et al, "Widespread siRNA 'off-target' transcript silencing mediated by see region sequence complementarity," RNA, 2006, pp. 1179-1187, vol. 12.
Birmingham, Amanda, et al., "3' UTR see matches, but not overall identity, are associated with RNAi off-targets," Nature Methods, 2006, pp. 199-204, vol. 3.
Lin, Xiaoyu, et al., "siRNA-mediated off-target gene silencing triggered by a 7 nt complementation," Nucleic Acids Research, 2005, pp. 4527-4535, vol. 33.
Anderson, Emily M et al., "Experimental validation of the importance of see complement frequency to siRNA specificity," RNA, 2008, pp. 853-861, vol. 14.
Jackson, Aimee L. et al., "Position-specific chemical modification of siRNAs reduces 'off-target' transcript silencing," RNA, 2006, pp. 1197-1205, vol. 12.
Puri, Nitin et al., "LNA® incorporated siRNAs exhibit lower off-target effects compared to 2'-OMethoxy in Cell Phenotypic Assays and Microarray Analysis," Nucleic Acids Symposium Series No. 52, 2008, pp. 25-26.
Dua, Pooja, et al., "Modified siRNA Structure With a Single Nucleotide Bulge Overcomes Conventional siRNA-mediated Off-target Silencing," Molecular Therapy, 2011, pp. 1676-1687, vol. 19.

\* cited by examiner

*Primary Examiner* — Kimberly Chong
(74) *Attorney, Agent, or Firm* — Tristan A. Fulerer; Moore & Van Allen, PLLC

(57) ABSTRACT

The present invention relates to a novel siRNA structure and the use thereof, and more particularly to a double-stranded siRNA molecule comprising an antisense strand and a sense strand, wherein the siRNA molecule has at least one single nucleotide bulge formed by introducing a single nucleotide into the antisense strand, particularly at position 2 from the 5' end, and to a method of using the same to silence a target gene. The siRNA molecule of the invention shows high target gene silencing efficiency while minimizing off-target effects caused by the antisense strand, and thus has improved target selectivity. Accordingly, the siRNA molecule of the invention can be substituted for conventional siRNA molecules and can be widely be used in siRNA-based gene silencing techniques, including gene therapy.

15 Claims, 18 Drawing Sheets

FIG. 1

| | | | | |
|---|---|---|---|---|
| si Survivin | AS 5' | UGAAAAUGUUGAUCUCCUU(dTdT) | SEQ ID NO: 1 | |
| | S 3' | (dTdT)ACUUUUACAACUAGAGGAA | SEQ ID NO: 2 | |
| si Survivin-2 | AS 5' | UAGAAAAUGUUGAUCUCCUU(dTdT) | SEQ ID NO: 3 | |
| | S 3' | (dTdT)A*CUUUUACAACUAGAGGAA | SEQ ID NO: 2 | |
| si Survivin-3 | AS 5' | UGAAAAAUGUUGAUCUCCUU(dTdT) | SEQ ID NO: 4 | |
| | S 3' | (dTdT)AC*UUUUACAACUAGAGGAA | SEQ ID NO: 2 | |
| si Survivin-4 | AS 5' | UGAAAAAUGUUGAUCUCCUU(dTdT) | SEQ ID NO: 5 | |
| | S 3' | (dTdT)ACU*UUUACAACUAGAGGAA | SEQ ID NO: 2 | |
| si Survivin-5 | AS 5' | UGAAAAAUGUUGAUCUCCUU(dTdT) | SEQ ID NO: 6 | |
| | S 3' | (dTdT)ACUU*UUACAACUAGAGGAA | SEQ ID NO: 2 | |
| si Survivin-16 | AS 5' | UGAAAAUGUUGAUCUCCUU(dTdT) | SEQ ID NO: 7 | |
| | S 3' | (dTdT)ACUUUUACAACUAGA*GGAA | SEQ ID NO: 2 | |
| si Survivin-17 | AS 5' | UGAAAAUGUUGAUCUCCUU(dTdT) | SEQ ID NO: 8 | |
| | S 3' | (dTdT)ACUUUUACAACUAGAG*GAA | SEQ ID NO: 2 | |
| si Survivin-18 | AS 5' | UGAAAAUGUUGAUCUCCUU(dTdT) | SEQ ID NO: 9 | |
| | S 3' | (dTdT)ACUUUUACAACUAGAGG*AA | SEQ ID NO: 2 | |
| si Survivin-19 | AS 5' | UGAAAAUGUUGAUCUCCUU(dTdT) | SEQ ID NO: 10 | |
| | S 3' | (dTdT)ACUUUUACAACUAGAGGA*A | SEQ ID NO: 2 | |

FIG. 4

| | | | |
|---|---|---|---|
| siSurvivin | AS 5' | UGAAAAUGUUGAUCUCCUU (dTdT) | SEQ ID NO: 1 |
| | S 3' | (dTdT) ACUUUUACAACUAGAGGAA | SEQ ID NO: 2 |
| | | | |
| siSurvivin-2'A' | AS 5' | U&GAAAAUGUUGAUCUCCUU (dTdT) | SEQ ID NO: 3 |
| | S 3' | (dTdT) A*CUUUUACAACUAGAGGAA | SEQ ID NO: 2 |
| | | | |
| siSurvivin-2'C' | AS 5' | UC̄GAAAAUGUUGAUCUCCUU (dTdT) | SEQ ID NO: 22 |
| | S 3' | (dTdT) A*CUUUUACAACUAGAGGAA | SEQ ID NO: 2 |
| | | | |
| siSurvivin-2'OMe | AS 5' | UGAAAAUGUUGAUCUCCUU (dTdT) | SEQ ID NO: 23 |
| | S 3' | (dTdT) ACUUUUACAACUAGAGGAA | SEQ ID NO: 2 |

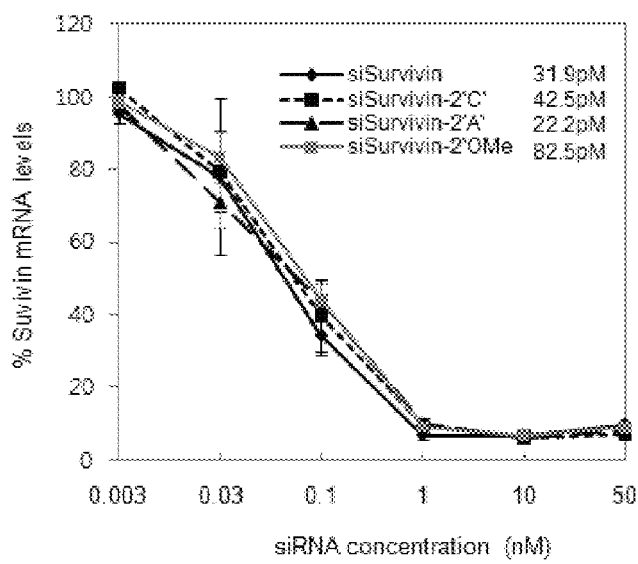

FIG. 5

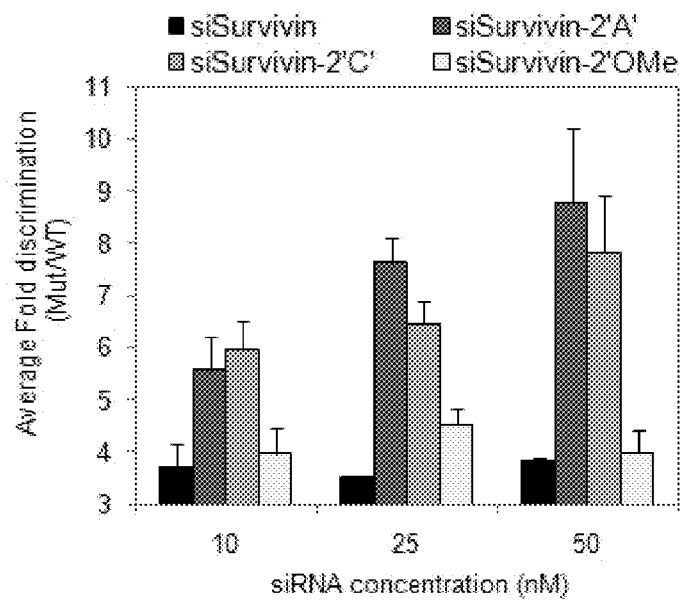

| siMPHOSPH1 | AS 5' | CUAGUGUCAUUCGCAUGUC(dTdT) | 3' | SEQ ID NO: 24 |
| | S 3' (dTdT)GAUCAGACUAAGCGUACAG | | 5' | SEQ ID NO: 25 |

| siMPHOSPH1-2'A' | AS 5' | CAUAGUGUCAUUCGCAUGUC(dTdT) | 3' | SEQ ID NO: 26 |
| | S 3' (dTdT)G AUCAGACUAAGCGUACAG | | 5' | SEQ ID NO: 25 |

| siMPHOSPH1-2'G' | AS 5' | CGUAGUGUCAUUCGCAUGUC(dTdT) | 3' | SEQ ID NO: 27 |
| | S 3' (dTdT)G AUCAGACUAAGCGUACAG | | 5' | SEQ ID NO: 25 |

| siMPHOSPH1-2'OMe | AS 5' | CUAGUGUCAUUCGCAUGUC(dTdT) | 3' | SEQ ID NO: 28 |
| | S 3' (dTdT)GAUCAGACUAAGCGUACAG | | 5' | SEQ ID NO: 25 |

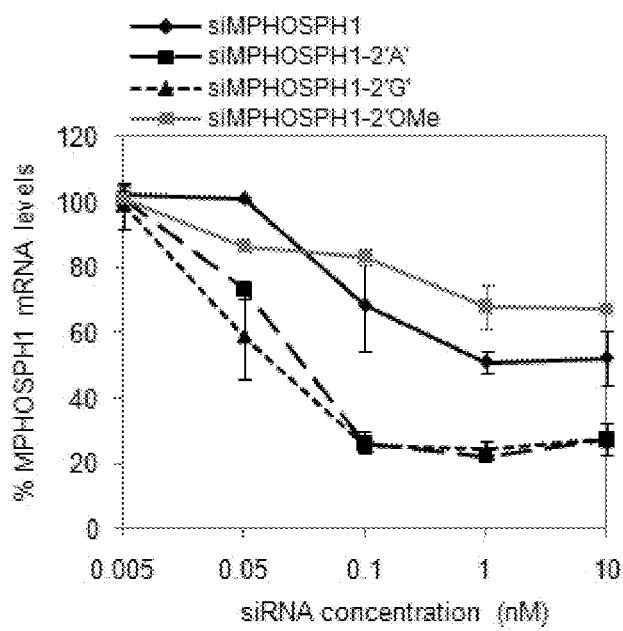

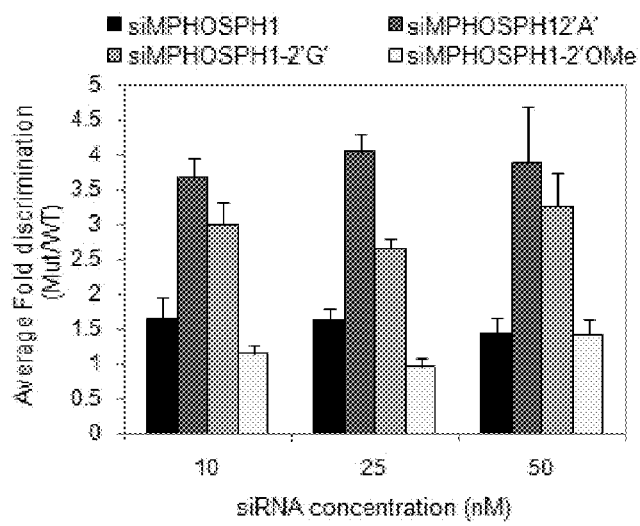

| siMAPK14 | AS 5' | AACCGCAGUUCUCUGUAGG(dTdT) 3' | SEQ ID NO: 32 |
| --- | --- | --- | --- |
| | S 3' (dTdT)UUGGCGUCAAGAGACAUCC | 5' | SEQ ID NO: 33 |
| siMAPK14-2'G' | AS 5' | AGACCGCAGUUCUCUGUAGG(dTdT) 3' | SEQ ID NO: 34 |
| | S 3' (dTdT)U UGGCGUCAAGAGACAUCC | 5' | SEQ ID NO: 33 |
| siMAPK14-2'C' | AS 5' | ACACCGCAGUUCUCUGUAGG(dTdT) 3' | SEQ ID NO: 35 |
| | S 3' (dTdT)U UGGCGUCAAGAGACAUCC | 5' | SEQ ID NO: 33 |
| siMAPK14-2'OMe | AS 5' | AACCGCAGUUCUCUGUAGG(dTdT) 3' | SEQ ID NO: 36 |
| | S 3' (dTdT)UUGGCGUCAAGAGACAUCC | 5' | SEQ ID NO: 33 |

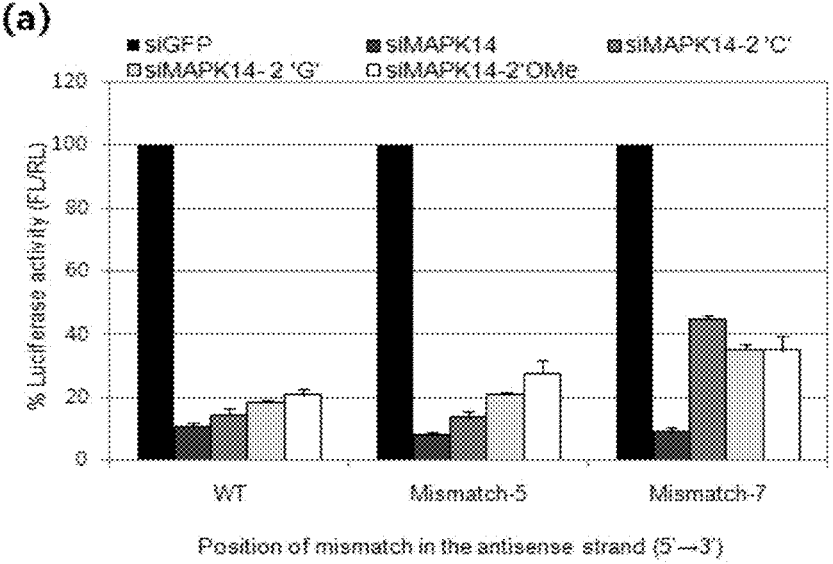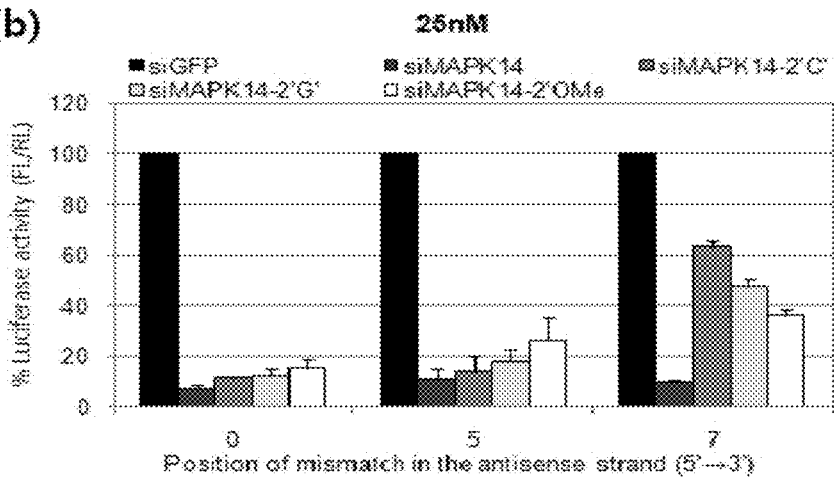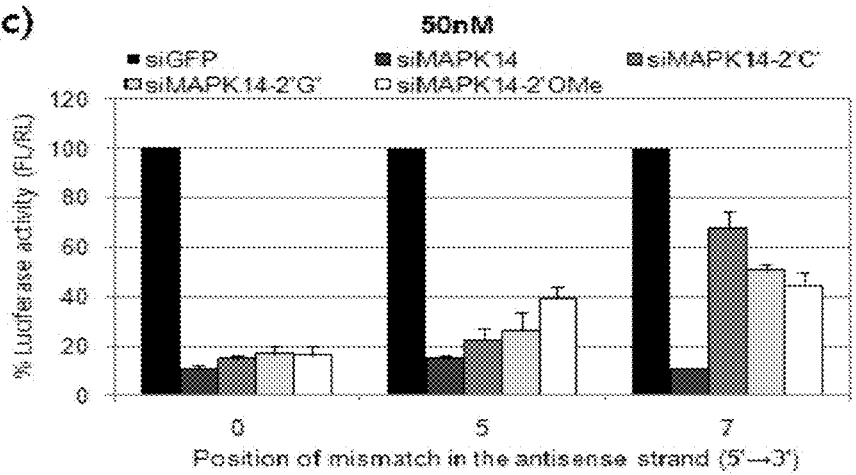
FIG. 14

FIG. 19

| | | | |
|---|---|---|---|
| siSurvivin | AS 5' | UGAAAAUGUUGAUCUCCUU(dTdT) 3' | SEQ ID NO: 1 |
| | S 3' | (dTdT)ACUUUUACAACUAGAGGAA 5' | SEQ ID NO: 2 |
| siSurvivin-Fork | AS 5' | UGAAAAUGUUGAUCUCCUU(dTdT) 3' | SEQ ID NO: 1 |
| | S 3' | UUUUUUACAACUAGAGGAA 5' | SEQ ID NO: 44 |
| siMAPK14 | AS 5' | AACCGCAGUUCUCUGUAGG(dTdT) 3' | SEQ ID NO: 32 |
| | S 3' | (dTdT)UUGGCGUCAAGAGACAUCC 5' | SEQ ID NO: 33 |
| siMAPK14-Fork | AS 5' | AACCGCAGUUCUCUGUAGG(dTdT) 3' | SEQ ID NO: 32 |
| | S 3' | AAGGCGUCAAGAGACAUCC 5' | SEQ ID NO: 45 |
| siMPHOSPH1 | AS 5' | CUAGUGUCAUUCGCAUGUC(dTdT) 3' | SEQ ID NO: 24 |
| | S 3' | (dTdT)GAUCAGACUAAGCGUACAG 5' | SEQ ID NO: 25 |
| siMPHOSPH1-Fork | AS 5' | CUAGUGUCAUUCGCAUGUC(dTdT) 3' | SEQ ID NO: 24 |
| | S 3' | UUUCAGACUAAGCGUACAG 5' | SEQ ID NO: 46 |

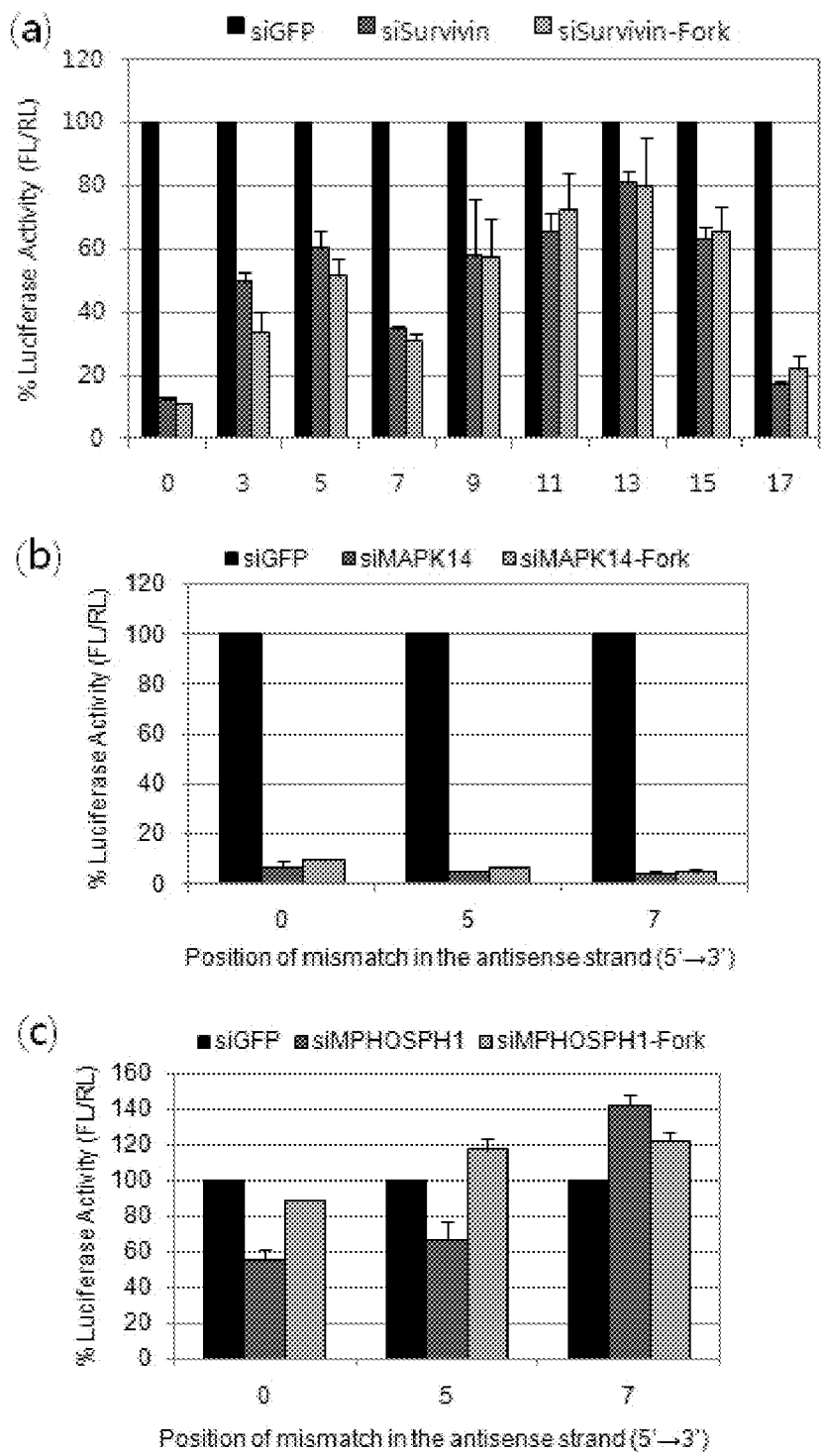

US 9,260,470 B2

```
SEQUENCE LISTING

<160> NUMBER OF SEQ ID NOS: 46

<210> SEQ ID NO 1
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: deoxyribonucleotides

<400> SEQUENCE: 1
ugaaaauguu gaucuccuut t                                            21

<210> SEQ ID NO 2
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: deoxyribonucleotides

<400> SEQUENCE: 2
aaggagauca acauuuucat t                                            21

<210> SEQ ID NO 3
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: ribonucleotides
<220> FEATURE:
<221> NAME/KEY: misc_feature
<222> LOCATION: (21)..(22)
<223> OTHER INFORMATION: deoxyribonucleotides

<400> SEQUENCE: 3
uagaaaaugu ugaucuccuu tt                                           22
```

```
<210> SEQ ID NO 4
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: ribonucleotides
<220> FEATURE:
<221> NAME/KEY: misc_feature
<222> LOCATION: (21)..(22)
<223> OTHER INFORMATION: deoxyribonucleotides

<400> SEQUENCE: 4
uguaaaaugu ugaucuccuu tt                                              22

<210> SEQ ID NO 5
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: ribonucleotides
<220> FEATURE:
<221> NAME/KEY: misc_feature
<222> LOCATION: (21)..(22)
<223> OTHER INFORMATION: deoxyribonucleotides

<400> SEQUENCE: 5
ugauaaaugu ugaucuccuu tt                                              22

<210> SEQ ID NO 6
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: ribonucleotides
<220> FEATURE:
<221> NAME/KEY: misc_feature
<222> LOCATION: (21)..(22)
<223> OTHER INFORMATION: deoxyribonucleotides

<400> SEQUENCE: 6
ugaauaaugu ugaucuccuu tt                                              22

<210> SEQ ID NO 7
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: ribonucleotides
<220> FEATURE:
<221> NAME/KEY: misc_feature
<222> LOCATION: (21)..(22)
<223> OTHER INFORMATION: deoxyribonucleotides

<400> SEQUENCE: 7
ugaaaauguu gaucugccuu tt                                              22
```

```
<210> SEQ ID NO 8
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: ribonucleotides
<220> FEATURE:
<221> NAME/KEY: misc_feature
<222> LOCATION: (21)..(22)
<223> OTHER INFORMATION: deoxyribonucleotides

<400> SEQUENCE: 8
ugaaaauguu gaucucgcuu tt                                              22

<210> SEQ ID NO 9
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: ribonucleotides
<220> FEATURE:
<221> NAME/KEY: misc_feature
<222> LOCATION: (21)..(22)
<223> OTHER INFORMATION: deoxyribonucleotides

<400> SEQUENCE: 9
ugaaaauguu gaucuccguu tt                                              22

<210> SEQ ID NO 10
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: ribonucleotides
<220> FEATURE:
<221> NAME/KEY: misc_feature
<222> LOCATION: (21)..(22)
<223> OTHER INFORMATION: deoxyribonucleotides

<400> SEQUENCE: 10
ugaaaauguu gaucuccugu tt                                              22

<210> SEQ ID NO 11
<211> LENGTH: 19
<212> TYPE: RNA
<213> ORGANISM: Artificial Sequence
<220> FEATURE:
<223> OTHER INFORMATION: Synthetic Construct

<400> SEQUENCE: 11
ggcuacgucc aggagcgca                                                  19

<210> SEQ ID NO 12
<211> LENGTH: 18
<212> TYPE: RNA
<213> ORGANISM: Artificial Sequence
<220> FEATURE:
```

```
<223> OTHER INFORMATION: Synthetic Construct

<400> SEQUENCE: 12
ugcguccugg acguagcc                                                        18

<210> SEQ ID NO 13
<211> LENGTH: 25
<212> TYPE: DNA
<213> ORGANISM: Artificial Sequence
<220> FEATURE:
<223> OTHER INFORMATION: Synthetic Construct

<400> SEQUENCE: 13
ctagtaagga gatcaacatt ttcaa                                                25

<210> SEQ ID NO 14
<211> LENGTH: 25
<212> TYPE: DNA
<213> ORGANISM: Artificial Sequence
<220> FEATURE:
<223> OTHER INFORMATION: Synthetic Construct

<400> SEQUENCE: 14
ctagtaagga gatcaacatt tccaa                                                25

<210> SEQ ID NO 15
<211> LENGTH: 25
<212> TYPE: DNA
<213> ORGANISM: Artificial Sequence
<220> FEATURE:
<223> OTHER INFORMATION: Synthetic Construct

<400> SEQUENCE: 15
ctagtaagga gatcaacatc ttcaa                                                25

<210> SEQ ID NO 16
<211> LENGTH: 25
<212> TYPE: DNA
<213> ORGANISM: Artificial Sequence
<220> FEATURE:
<223> OTHER INFORMATION: Synthetic Construct

<400> SEQUENCE: 16
ctagtaagga gatcaacctt ttcaa                                                25

<210> SEQ ID NO 17
<211> LENGTH: 25
<212> TYPE: DNA
<213> ORGANISM: Artificial Sequence
<220> FEATURE:
<223> OTHER INFORMATION: Synthetic Construct

<400> SEQUENCE: 17
ctagtaagga gatcaccatt ttcaa                                                25

<210> SEQ ID NO 18
<211> LENGTH: 25
<212> TYPE: DNA
<213> ORGANISM: Artificial Sequence
<220> FEATURE:
<223> OTHER INFORMATION: Synthetic Construct

<400> SEQUENCE: 18
ctagtaagga gatgaacatt ttcaa                                                25
```

```
<210> SEQ ID NO 19
<211> LENGTH: 25
<212> TYPE: DNA
<213> ORGANISM: Artificial Sequence
<220> FEATURE:
<223> OTHER INFORMATION: Synthetic Construct

<400> SEQUENCE: 19
ctagtaagga gctcaacatt ttcaa                                              25

<210> SEQ ID NO 20
<211> LENGTH: 25
<212> TYPE: DNA
<213> ORGANISM: Artificial Sequence
<220> FEATURE:
<223> OTHER INFORMATION: Synthetic Construct

<400> SEQUENCE: 20
ctagtaaggc gatcaacatt ttcaa                                              25

<210> SEQ ID NO 21
<211> LENGTH: 25
<212> TYPE: DNA
<213> ORGANISM: Artificial Sequence
<220> FEATURE:
<223> OTHER INFORMATION: Synthetic Construct

<400> SEQUENCE: 21
ctagtaatga gatcaacatt ttcaa                                              25

<210> SEQ ID NO 22
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: ribonucleotides
<220> FEATURE:
<221> NAME/KEY: misc_feature
<222> LOCATION: (21)..(22)
<223> OTHER INFORMATION: deoxyribonucleotides

<400> SEQUENCE: 22
ucgaaaaugu ugaucuccuu tt                                                 22

<210> SEQ ID NO 23
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(19)
<223> OTHER INFORMATION: ribonucleotides
<220> FEATURE:
<221> NAME/KEY: misc_feature
<222> LOCATION: (2)..(2)
<223> OTHER INFORMATION: 2'OMe modified nucleotide
<220> FEATURE:
<221> NAME/KEY: misc_feature
<222> LOCATION: (20)..(21)
<223> OTHER INFORMATION: deoxyribonucleotides

<400> SEQUENCE: 23
ugaaaauguu gaucuccuut t                                                  21
```

```
<210> SEQ ID NO 24
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: deoxyribonucleotides

<400> SEQUENCE: 24
cuagugucau ucgcauguct t                                              21

<210> SEQ ID NO 25
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: deoxyribonucleotides

<400> SEQUENCE: 25
gacaugcgaa ucagacuagt t                                              21

<210> SEQ ID NO 26
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: ribonucleotides
<220> FEATURE:
<221> NAME/KEY: misc_feature
<222> LOCATION: (21)..(22)
<223> OTHER INFORMATION: deoxyribonucleotides

<400> SEQUENCE: 26
cauaguguca uucgcauguc tt                                             22

<210> SEQ ID NO 27
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: ribonucleotides
<220> FEATURE:
<221> NAME/KEY: misc_feature
<222> LOCATION: (21)..(22)
<223> OTHER INFORMATION: deoxyribonucleotides

<400> SEQUENCE: 27
cguaguguca uucgcauguc tt                                             22
```

<210> SEQ ID NO 28
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(19)
<223> OTHER INFORMATION: ribonucleotides
<220> FEATURE:
<221> NAME/KEY: misc_feature
<222> LOCATION: (2)..(2)
<223> OTHER INFORMATION: 2'OMe modified nucleotide
<220> FEATURE:
<221> NAME/KEY: misc_feature
<222> LOCATION: (20)..(21)
<223> OTHER INFORMATION: deoxyribonucleotides

<400> SEQUENCE: 28
cuagugucau ucgcauguct t                                      21

<210> SEQ ID NO 29
<211> LENGTH: 25
<212> TYPE: DNA
<213> ORGANISM: Artificial Sequence
<220> FEATURE:
<223> OTHER INFORMATION: Synthetic Construct

<400> SEQUENCE: 29
ctagtgacat gcgaatgaca ctaga                                  25

<210> SEQ ID NO 30
<211> LENGTH: 25
<212> TYPE: DNA
<213> ORGANISM: Artificial Sequence
<220> FEATURE:
<223> OTHER INFORMATION: Synthetic Construct

<400> SEQUENCE: 30
ctagtgacat gcgaatgact ctaga                                  25

<210> SEQ ID NO 31
<211> LENGTH: 25
<212> TYPE: DNA
<213> ORGANISM: Artificial Sequence
<220> FEATURE:
<223> OTHER INFORMATION: Synthetic Construct

<400> SEQUENCE: 31
ctagtgacat gcgaatgtca ctaga                                  25

<210> SEQ ID NO 32
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: deoxyribonucleotides

<400> SEQUENCE: 32
aaccgcaguu cucuguaggt t                                               21

<210> SEQ ID NO 33
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: deoxyribonucleotides

<400> SEQUENCE: 33
ccuacagaga acugcgguut t                                               21

<210> SEQ ID NO 34
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: ribonucleotides
<220> FEATURE:
<221> NAME/KEY: misc_feature
<222> LOCATION: (21)..(22)
<223> OTHER INFORMATION: deoxyribonucleotides

<400> SEQUENCE: 34
agaccgcagu ucucuguagg tt                                              22

<210> SEQ ID NO 35
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: ribonucleotides
<220> FEATURE:
<221> NAME/KEY: misc_feature
<222> LOCATION: (21)..(22)
<223> OTHER INFORMATION: deoxyribonucleotides

<400> SEQUENCE: 35
acaccgcagu ucucuguagg tt                                              22

<210> SEQ ID NO 36
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(19)
<223> OTHER INFORMATION: ribonucleotides
<220> FEATURE:
<221> NAME/KEY: misc_feature
<222> LOCATION: (2)..(2)
<223> OTHER INFORMATION: 2'OMe modified nucleotide
<220> FEATURE:
<221> NAME/KEY: misc_feature

```
<222> LOCATION: (20)..(21)
<223> OTHER INFORMATION: deoxyribonucleotides

<400> SEQUENCE: 36
aaccgcaguu cucuguaggt t                                              21

<210> SEQ ID NO 37
<211> LENGTH: 25
<212> TYPE: DNA
<213> ORGANISM: Artificial Sequence
<220> FEATURE:
<223> OTHER INFORMATION: Synthetic Construct

<400> SEQUENCE: 37
ctagtcctac agagaactgc ggtta                                          25

<210> SEQ ID NO 38
<211> LENGTH: 25
<212> TYPE: DNA
<213> ORGANISM: Artificial Sequence
<220> FEATURE:
<223> OTHER INFORMATION: Synthetic Construct

<400> SEQUENCE: 38
ctagtcctac agagaactgt ggtta                                          25

<210> SEQ ID NO 39
<211> LENGTH: 25
<212> TYPE: DNA
<213> ORGANISM: Artificial Sequence
<220> FEATURE:
<223> OTHER INFORMATION: Synthetic Construct

<400> SEQUENCE: 39
ctagtcctac agagaacagc ggtta                                          25

<210> SEQ ID NO 40
<211> LENGTH: 19
<212> TYPE: RNA
<213> ORGANISM: Artificial Sequence
<220> FEATURE:
<223> OTHER INFORMATION: Synthetic Construct

<400> SEQUENCE: 40
ugaaaauguu gaucuccuu                                                 19

<210> SEQ ID NO 41
<211> LENGTH: 16
<212> TYPE: RNA
<213> ORGANISM: Artificial Sequence
<220> FEATURE:
<223> OTHER INFORMATION: Synthetic Construct

<400> SEQUENCE: 41
gagaucaaca uuuuca                                                    16

<210> SEQ ID NO 42
<211> LENGTH: 20
<212> TYPE: RNA
<213> ORGANISM: Artificial Sequence
<220> FEATURE:
<223> OTHER INFORMATION: Synthetic Construct

<400> SEQUENCE: 42
ucgaaaaugu ugaucuccuu                                                20
```

<210> SEQ ID NO 43
<211> LENGTH: 25
<212> TYPE: DNA
<213> ORGANISM: Artificial Sequence
<220> FEATURE:
<223> OTHER INFORMATION: Synthetic Construct

<400> SEQUENCE: 43
ctagttgaaa atgttgatct cctta                                            25

<210> SEQ ID NO 44
<211> LENGTH: 19
<212> TYPE: RNA
<213> ORGANISM: Artificial Sequence
<220> FEATURE:
<223> OTHER INFORMATION: Synthetic Construct

<400> SEQUENCE: 44
aaggagauca acauuuuuu                                                   19

<210> SEQ ID NO 45
<211> LENGTH: 19
<212> TYPE: RNA
<213> ORGANISM: Artificial Sequence
<220> FEATURE:
<223> OTHER INFORMATION: Synthetic Construct

<400> SEQUENCE: 45
ccuacagaga acugcggaa                                                   19

<210> SEQ ID NO 46
<211> LENGTH: 19
<212> TYPE: RNA
<213> ORGANISM: Artificial Sequence
<220> FEATURE:
<223> OTHER INFORMATION: Synthetic Construct

<400> SEQUENCE: 46
gacaugcgaa ucagacuuu                                                   19

SIRNA STRUCTURE FOR MINIMIZING OFF-TARGET EFFECTS CAUSED BY ANTISENSE STRANDS, AND USE THEREOF

CROSS-REFERENCE TO RELATED APPLICATIONS

This application is filed under the provisions of 35 U.S.C. §371 and claims the priority of International Patent Application No. PCT/KR2010/007771 filed on 4 Nov. 2010 entitled "Novel SIRNA Structure for Minimizing Off-Target Effects Caused by Antisense Strands, and Use Thereof" in the name of Dong Ki LEE, et al., which claims priority to Korean Patent Application No. 10-009-0105808 filed on 4 Nov. 2009, both of which are hereby incorporated by reference herein in their entirety.

TECHNICAL FIELD

The present invention relates to a novel siRNA structure and the use thereof, and more particularly to a novel siRNA molecule, which shows high target gene silencing efficiency while minimizing off-target effects caused by the antisense strand, and to a method of using the same to silence a target gene.

BACKGROUND ART

Off-target silencing is a major concern when using RNA interference (RNAi). Conventional 19+2 siRNA structures can undergo imperfect pairing of the antisense strand with mRNA targets or incorporation of the sense strand into RISC complexes, which results in unintended cleavage of targets. Thus, such conventional 19+2 siRNA structures show considerable non-specific silencing (Jackson, A. L. & Linsley, P. S., *Trends Genet.*, 20(11): 521, 2004). A recent study conducted by the present inventor has reported an asymmetric siRNA (16+3A structure) having a shortened sense strand (Chang C. I. et al., *Mol. Ther.*, 17(4): 725, 2009). This asiRNA structure overcomes the problems associated with the 19+2 siRNA structure, such as sense strand-mediated silencing and RNAi machinery saturation. Many other researchers have also reported various siRNA modifications that reduce sense-strand-mediated non-specific silencing (Elmen, J., et al., *Nucleic Acids Res.*, 33(1): 439, 2005; Sano, M., et al., *Nucleic Acids Res.*, 36(18): 5812, 2008; Sun, X., et al., *Nat. Biotechnol.*, 26(12): 1379, 2008). However, as compared to such studies, studies on the reduction in antisense-mediated off-target silencing were extremely small.

Jackson et al. first demonstrated that siRNA-mediated gene silencing is sequence-dependent rather than target-dependent (Jackson, A. L., et al., *Nat. Biotechnol.*, 21(6): 635, 2003; Jackson, A. L., et al., *Rna*, 12(7): 1179, 2006b). Additionally, initiation of target cleavage by RISC is caused by limited complementarity between RNA double strands and transcripts. Birmingham et al. demonstrated that unintended pairing of the 3' UTR of transcripts with the seed region of siRNA is the major cause of off-target effects (Birmingham et al., *Nat. Methods*, 3(3): 199, 2006). Pairing between the hexamer seed region of an siRNA guide strand (e.g., nucleotides 2-7) and complementary sequences in the 3' UTR of mature transcripts is a primary determinant of off-target gene regulation (Lin et al., *Nucleic Acids Res.*, 33(14): 4527, 2005; Anderson et al., *Rna*, 14(5): 853, 2008). Such off-targets can induce a measurable amount of phenotypic changes that can account for up to 30% of the positive hits in RNAi based phenotypic screens. In view of widespread off-target silencing mediated by conventional siRNAs having a 19+2 structure, any chemical or structural modification of the siRNA backbone, which can reduce off-target silencing while maintaining intended silencing efficiency, is a great concern.

A collaborative study between Dharmacon Research (Lafayette, Colo.) and Rosetta Inpharmatics (Seattle, Wash.) demonstrated that methyl-groups added to the 2' position of the ribosyl ring of the nucleotide at a specific position in the siRNA guide strand significantly reduced siRNA-mediated off-target effects (Jackson et al., *Rna*, 12(7): 1197, 2006). Additionally, it was found that chemical modification of the base at position 2 in the guide strand was most effective in reducing both the number and extent of off-target effects without significantly influencing the silencing of an intended target. However, Ambion Inc. compared a 2'OMe-modified siRNA with an LNA-modified siRNA and found that the LNA-modified siRNA was superior in reducing off-target effects mediated by the antisense strand (Puri et al., *Nucleic Acids Symp. Ser.* 2008). However, it was shown that such chemical modifications successfully reduced the antisense off-target effects of siRNA, while some among them, such as 2'-OMe, could also reduce on-target silencing efficiency. Furthermore, such chemical modification strategies could not be applied to siRNAs which are expressed in cells.

Accordingly, the present inventors have made extensive efforts to provide a novel siRNA structure, which has high gene silencing efficiency while minimizing off-target effects caused by the antisense strand, and as a result, have found that a novel siRNA molecular structure constructed by the present inventors has excellent gene silencing effects without showing off-target effects caused by the antisense strand, and thus has improved target selectivity, thereby completing the present invention.

DISCLOSURE OF INVENTION

It is a main object of the present invention to provide a novel siRNA complex which has improved target selectivity without showing off-target effects caused by the antisense strand.

To achieve the above object, the present invention provides a double-stranded siRNA molecule comprising an antisense strand and a sense strand complementary to the antisense strand, wherein the siRNA molecule has at least one single nucleotide bulge formed by introducing a single nucleotide into the antisense strand.

The present invention also provides a gene silencing composition containing said siRNA molecule.

The present invention also provides the use of said siRNA molecule for gene silencing.

The present invention also the use of said siRNA molecule for suppressing off-target effects caused by the antisense strand of siRNA molecules.

The present invention also provides a gene silencing kit containing said siRNA molecule.

The present invention also provides a method for silencing a target gene in a cell, the method comprising a step of introducing said siRNA molecule into the cell.

The present invention also provides a method for silencing a target gene in a cell, the method comprising a step of expressing said siRNA molecule in the cell.

The present invention also provides a method for suppressing off-target effects caused by the antisense strand of siRNA molecules, the method comprising a step of introducing said siRNA molecule into a cell.

The present invention also provides a method for suppressing off-target effects caused by the antisense strand of siRNA molecules, the method comprising a step of expressing said siRNA molecule in a cell.

Other features and embodiments of the present invention will be more apparent from the following detailed descriptions and the appended claims

BRIEF DESCRIPTION OF THE DRAWINGS

FIG. 1 shows an siRNA for Survivin and siRNAs prepared to have a single nucleotide bulge at each of positions 2, 3, 4, 5, 16, 17, 18 and 19 from the 5' end of the antisense strand.

FIG. 4 shows siRNAs which are siSurvivin, siSurvivin-2 'A', siSurvivin-2 'C' and siSurvivin-2'OMe.

FIG. 5 is a graphic diagram showing the $IC_{50}$ values of siRNAs, which are siSurvivin, siSurvivin-2 'A', siSurvivin-2 'C' and siSurvivin-2'OMe, for endogenous Survivin mRNA.

FIG. 6a shows the results obtained using 10 nM of each siRNA; FIG. 6b shows the results obtained using 25 nM of each siRNA; and FIG. 6c shows the results obtained using 50 nM of each siRNA.

FIG. 7 is a graphic diagram showing the average ratio of luciferase activity between wild type and mismatched targets for siRNAs of FIG. 4.

FIG. 8 shows siRNA which are siMPHOSPH1, siMPHOSPH1-2 'A', siMPHOSPH1-2 'G' and siMPHOSPH1-2'OMe.

FIG. 9 is a graphic diagram showing the $IC_{50}$ values of siRNAs, which are siMPHOSPH1, siMPHOSPH1-2 'A', siMPHOSPH1-2 'G' and siMPHOSPH1-2'OMe, for endogenous MPHOSPH1 mRNA.

FIG. 10a shows the results obtained using 10 nM of each siRNA; FIG. 10b shows the results obtained using 25 nM of each siRNA; and FIG. 10c shows the results obtained using 50 nM of each siRNA.

FIG. 11 is a graphic diagram showing the average ratio of luciferase activity between wild type and mismatched targets for the siRNAs of FIG. 8.

FIG. 12 shows siRNAs which are siMAPK14, siMAPK14-2 'G', siMAPK14-2 'C' and siMAPK14-2'OMe.

FIG. 14 is a set of graphs showing luciferase activities measured to determine the off-target silencing effects of siRNAs of FIG. 12 for MAPK14 antisense targets (WT) and mismatched targets (siGFP: control). Specifically, FIG. 14a shows the results obtained using 10 nM of each siRNA; FIG. 14b shows the results obtained using 25 nM of each siRNA; and FIG. 14c shows the results using 50 nM of each siRNA.

FIG. 19 shows the structures of siRNAs and fork-siRNAs.

FIG. 20 is a set of graphs showing luciferase activities measured to determine the off-target silencing effects of the siRNAs and fork-siRNAs of FIG. 19 (siGFP: control).

FIGS. 23A to 23C are MA plots showing the changes in expression for transcripts (red points) having homology with the antisense seed region, transcripts (yellow points) having homology with the modified antisense seed region, and other transcripts (gray points), which result from treatment with siSurvivin (A), siSurvivin-2'C' (B) and siSurvivin-2'OMe (C); FIGS. 23D to 23F are graphic diagrams showing fold changes ($\log_2$) determine to evaluate expression levels resulting from treatment with siSurvivin (D), siSurvivin-2'C' (E) and siSurvivin-2'OMe (F); FIG. 23G is a graphic diagram showing the number of off-targets; and FIG. 23H is a graphic diagram showing a siRNA-mediated reduction in off-target silencing.

BEST MODE FOR CARRYING OUT THE INVENTION

Figure 2:
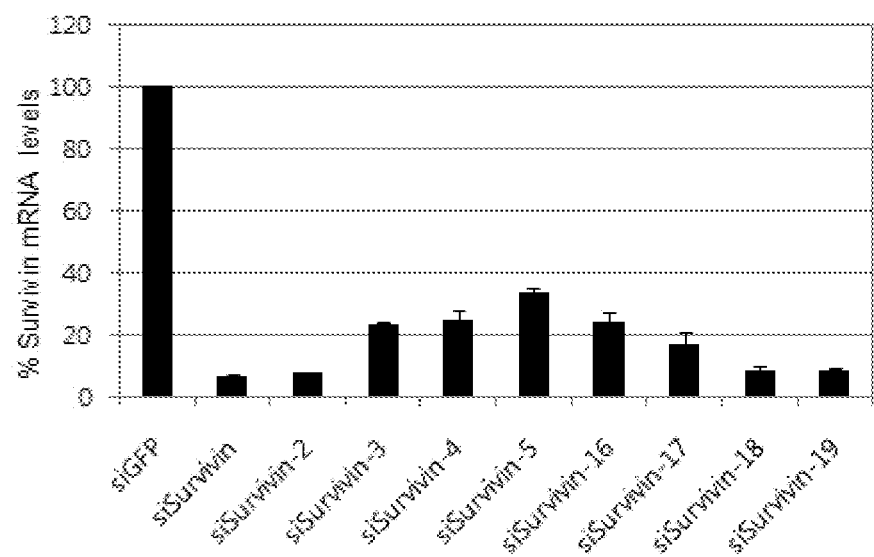
FIG. 2 is a graphic diagram showing the off-target silencing effects of the siRNAs of FIG. 1, determined by measuring luciferase activity.

Unless otherwise defined, all technical and scientific terms used herein have the same meaning as commonly understood by one of ordinary skill in the art. Generally, the nomenclature used herein are well known and conventionally used in the art.

The definition of main terms used in the detailed description of the invention is as follows.

As used herein, the term "siRNA (small interfering RNA)" means a short double-stranded RNA (dsRNA) that mediates efficient gene silencing in a sequence-specific manner.

As used herein, the phrase "antisense strand" refers to a polynucleotide that is substantially or 100% complementary to a target nucleic acid of interest. For example, an antisense strand may be complementary, in whole or in part, to a molecule of messenger RNA, an RNA sequence that is not mRNA (e.g., microRNA, piwiRNA, tRNA, rRNA and hnRNA) or a sequence of DNA that is either coding or non-coding. The terms "antisense strand" and "guide strand" are used interchangeably herein.

As used herein, the phrase "sense strand" refers to a polynucleotide that has the same nucleotide sequence, in whole or in part, as a target nucleotide sequence of interest. For example, a sense strand has the same nucleotide sequence, in whole or in part, as a molecule of messenger RNA, an RNA sequence that is not mRNA (e.g., microRNA, piwiRNA, tRNA, rRNA and hnRNA) or a sequence of DNA that is either coding or non-coding.

As used herein, the term "gene" is intended to have the broadest meaning, and the gene can encode a structural protein or a regulatory protein. Herein, the regulatory protein includes a transcriptional factor, a heat shock proteins, or a protein that is involved in DNA/RNA replication, transcription and/or translation. Also, the target gene whose expression is to be inhibited is inherent in a viral genome, and may be integrated into the animal gene or may be present as an extrachromosomal element. For example, the target gene may be a gene on an HIV genome. In this case, siRNA molecule is useful in inactivating translation of the HIV gene in a mammalian cell.

As used herein, the phrase "off-target effects" refers to any instance in which the sense strand of siRNA causes unexpected other mRNA degradation or other gene silencing and also the antisense strand of siRNA causes unexpected other mRNA degradation or other gene silencing by being paired with unexpected target, even though siRNA is originally used to induce the degradation of mRNA having a sequence complementary to the antisense strand so as to obtain the effect of inhibiting the gene expression of the mRNA.

As used herein, the term "bulge" refers to a portion in a double-stranded nucleic acid, which is not paired and is gaped open due to the introduction of one or more nucleotides.

In one aspect, the present invention is directed to a double-stranded siRNA molecule comprising an antisense strand and a sense strand complementary to the antisense strand, wherein the siRNA molecule has at least one single nucleotide bulge formed by introducing a single nucleotide into the antisense strand.

The siRNA molecule of the present invention may be a molecule synthesized according to a general method, but the scope of the present invention is not limited thereto. Namely, in the present invention, the siRNA molecule may be chemically or enzymatically synthesized. The siRNA molecule of the present invention may be derived from naturally occurring genes by standard recombinant techniques, and in this case, the siRNA molecule may be substantially complementary at the nucleotide sequence level to at least a part of mRNA of the target gene, the expression of which is to be modified.

The siRNA molecule according to the present invention may comprise a chemical modification. The chemical modification may be the substitution of the hydroxyl group at position 2' of the ribose of at least one nucleotide included in the siRNA by any one of a hydrogen atom, a fluorine atom, an —O-alkyl group, an —O-acyl group and an amino group. In addition, the chemical modification may also be the substitution of the hydroxyl group by any one of —Br, —Cl, —R, —R'OR, —SH, —SR, —N3 and —CN(R=alkyl, aryl, or alkylene) in order to increase the ability to deliver the siRNA. Furthermore, the chemical modification may be the substitution of the phosphate backbone of at least one nucleotide by any one of a phosphorothioate form, a phosphorodithioate form, an alkylphosphonate form, a phosphoroamidate form and a boranophosphate form. Moreover, the chemical modification may be the substitution of at least one nucleotide included in the siRNA by any one of LNA (locked nucleic acid), UNA (unlocked nucleic acid), morpholino, and PNA (peptide nucleic acid). In addition, the chemical modification may be achieved by coupling the siRNA to one or more selected from the group consisting of lipids, cell penetrating peptides, and cell targeting ligands.

In the present invention, the single nucleotide bulge may be present in the 5' end region or 3' end region of the antisense strand of the siRNA, in which the 5' end region may comprise nucleotides at positions 2 to 4 from the 5' end, and the 3' end region may comprise nucleotides at positions 2 to 4 from the 3' end.

In the present invention, nucleotides which are introduced to form the bulge are not limited to particular bases, but are preferably nucleotides having a base different from that of nucleotides which are adjacent thereto after introduction. Alternatively, the nucleotides may be abasic nucleotides. This is necessary to avoid formation of ambiguous pairs with the adjacent nucleotides of the sense strand.

In the present invention, it was found that, when a bulge was formed by introducing a single nucleotide into the antisense strand of an siRNA, the target gene silencing efficiency of the modified siRNA was similar or superior to that of the original siRNA structure, while off-target effects caused by the antisense strand were minimized. In one example of the present invention, it was shown that, when a single nucleotide bulge was present at nucleotide positions 2-4 from the 5' end of the antisense strand of an siRNA or at nucleotide positions 17-19 from the 5' end (i.e., at positions 2-4 from the 3' end), the target gene silencing efficiency of the siRNA was excellent.

Meanwhile, in another example of the present invention, in order to examine whether off-target effects caused by the antisense strand are minimized, a test for measuring the efficiency of silencing of mismatch targets mutated by substitution for antisense targets was performed. As a result, it was shown that, when a single nucleotide bulge was formed at the second nucleotide position from the 5' end of the antisense strand of an siRNA, off-target effects were most efficiently suppressed. Accordingly, in the present invention, the single nucleotide bulge is preferably present at the second nucleotide position from the 5' end of the antisense strand of an siRNA.

In examples of the present invention, it was shown that, when the siRNA structure according to the present invention was applied to siRNAs which target not only Survivin, but also MPHOSPH1 and MAPK14, off-target effects caused by the antisense strand of the siRNAs were very efficiently minimized, and thus target selectivity was increased. Accordingly, it will be obvious to those skilled in the art that, even when siRNAs which target other genes are provided according to the present invention, these siRNAs can show the same results.

Meanwhile, in one example of the present invention, it was found that, when the present invention is applied to an asymmetric siRNA molecule found to reduce off-target effects caused by the sense strand, a very efficient siRNA molecule that minimizes off-target effects caused by both the sense and antisense strands could be provided. Accordingly, in the present invention, the siRNA molecule preferably comprises a 19-21-nucleotide (nt) antisense strand and a 13-17-nt sense strand having a sequence complementary to the antisense strand, wherein the 5' end of the antisense strand is a blunt end, and the 3' end of the antisense strand has an overhang. In order to prevent saturation of the RNAi machinery while minimizing off-target effects caused by the sense strand, the length of the sense strand in the siRNA molecule is preferably 15-16 nt, and the length of the overhang is preferably 3-6 nt. Alternatively, the length of the antisense strand may be 19 nt, and the length of the overhang may be 2-4 nt.

In addition, in another example of the present invention, genome wide expression profiling was performed in order to analyze the effect of the siRNA molecule according to the present invention on off-target silencing in cells. As a result, it could be seen that the siRNA molecule according to the present invention had significant off-target silencing effects in cells compared to non-modified siRNA molecules or other modified siRNA molecules.

In addition, the present invention suggests that the siRNA molecule according to the present invention has the effect of efficiently silencing a target gene. That is, in another aspect, the present invention is directed to a gene silencing composition containing said siRNA molecule.

The gene silencing composition according to the present invention may be provided in the form of a kit for inhibiting gene expression. The kit for inhibiting gene expression may take the form of bottles, tubs, sachets, envelops, tubes, ampoules, and the like, which may be formed in part or in whole from plastic, glass, paper, foil, wax, and the like. The container may be equipped with a fully or partially detachable lid that may initially be part of the container or may be affixed to the container by mechanical, adhesive, or other means. The container may also be equipped with a stopper, allowing access to the contents by a syringe needle. The kit may comprise an exterior package which may include instructions regarding the use of the components.

In still another aspect, the present invention is directed to a method for silencing a target gene in a cell using said siRNA molecule. That is, the present invention is directed to a method for silencing a target gene in a cell, the method comprising a step of introducing said siRNA molecule into the cell.

In the present invention, the antisense strand of the siRNA molecule may be complementary to the mRNA sequence of a target gene.

In the present invention, the target gene may be an endogeneous gene or a transgene.

Herein, the siRNA molecule according to the present invention is not limited to synthetic siRNA molecules and may also be applied to siRNA or shRNA, which is expressed in cells using an expression vector or the like, unlike conventional siRNA molecules having chemical modifications such as 2'-OMe or LNA known to have off-target effects. That is, the siRNA molecule according to the present invention may be expressed in a cell to silence the target gene. Therefore, in yet another aspect, the present invention is directed to a method for silencing a target gene in a cell, the method comprising a step of expressing said siRNA molecule in the cell.

Meanwhile, the siRNA molecule according to the present invention can be obtained by expression in cells. Therefore, in a further aspect, the present invention is directed to a method for expressing said siRNA molecule in cells.

In addition, the siRNA molecule according to the present invention minimizes off-target effects caused by the antisense strand of the siRNA molecule. In a still further aspect, the present invention is directed to a method for suppressing off-target effects caused by the antisense strand of siRNA molecules, the method comprising a step of introducing or expressing said siRNA molecule into a cell.

EXAMPLES

Hereinafter, the present invention will be described in further detail with reference to examples. It will be obvious to a person having ordinary skill in the art that these examples are illustrative purposes only and are not to be construed to limit the scope of the present invention. That is, the following steps will be described as one illustrative ones and do not limit the scope of the present invention.

The following examples particularly illustrate only siRNAs for Survivin, MPHOSPH1 and MAPK14 as target genes, but it will be obvious to those skilled in the art that, even when siRNAs which target other genes are provided, these siRNAs can show the same results.

Example 1

Comparison of Target Gene Silencing Effect Between siRNA Molecules Having Single Nucleotide Bulge and Conventional siRNA Molecules In order to compare antisense strand-mediated off-target effects between the siRNA molecules according to the present invention and conventional non-modified siRNA molecules, the following test was carried out.

First, as shown in FIG. 1, siRNAs having a single nucleotide bulge formed on the antisense strand were prepared to have the single nucleotide bulge at positions 2, 3, 4, 5, 16, 17, 18 and 19 from the 5' end of the antisense strand. In FIG. 1, the introduced single nucleotides are indicated by a red color, and the symbol * indicates the positions of the bulges. RNAs, which were synthesized chemically and separated from HPLC, were purchased from Samchully Pharma, Inc. and annealed according to the manufacturer's protocol.

For the siRNA molecules having the bulges and the original siRNA molecules, silencing of the antisense target in Hela cells (ATCC CCL-2) was tested in the following manner. As a control, siGFP was used.

```
siGFP
                                (SEQ ID NO: 11)
Sense        5'-GGCUACGUCCAGGAGCGCA-3'

(SEQ ID NO: 12)
Antisense    5'-UGCGUCCUGGACGUAGCC-3'
```

Specifically, 10 nM of siGFP, siSurvivin (non-modified original siRNA molecule) and the bulged siSurvivins of FIG. 1, together with a pMIR firefly luciferase vector having the antisense target sequence of siSurvivin, was transfected into Hela cells using Lipofectamine 2000 reagent (Invitrogen) according to the manufacturer's protocol.

The above vector was constructed by cloning a DNA oligonucleotide corresponding to the siSurvivin antisense target sequence into the SpeI and HindIII positions of the 3' UTR of a pMIR Report-luciferase vector (Ambion). The incorporated siSurvivin antisense target sequence was as follows:

```
siSurvivin antisense target oligo
                                (SEQ ID NO: 13)
5'-CTAGTAAGGAGATCAACATTTTCAA-3'
```

Hela cells were cultured in Dulbecco's modified Eagle's medium, supplemented with 10% FBS (fetal bovine serum), 100 U/ml penicillin and 100 μg/ml streptomycin. The cells were cultured in a 24-well plate for 24 hours, and when a confluence of 30-50% was reached, transfection was performed in antibiotic-free complete medium.

24 hours after the transfection, the cells were lysed using passive lysis buffer (Dual-luciferase Reporter Assay system;

Promega), and luciferase activity for 20 μl of each cell extract was measured using Victor3 plate reader (PerkinElmer). The firefly luciferase activity was normalized by *Renilla* luciferase activity for each well, and the silencing efficiency of each siRNA structure was calculated by normalization of the luciferase activity of the siGFP-transfected sample. All the tests were repeated three times.

As a result, as can be seen in FIG. 2, the silencing effects of the siRNA molecules having the single nucleotide bulge decreased in a position-dependent manner. Specifically, the siRNAs having the single nucleotide bulge at positions 2 and 19 from the 5' end of the antisense strand had substantially the same silencing efficiency as conventional siSurvivin having no mutation. Furthermore, the siRNA having the single nucleotide bulge at position 18 showed a silencing efficiency of 80% or higher. In addition, it can be seen that the siRNAs having the single nucleotide bulge at positions 3, 4 and 17 showed silencing efficiency lower than the siRNAs having the single nucleotide bulge at positions 2, 18 and 19, but had significant silencing effects compared to the siRNAs having the bulge at positions 5 and 16.

Thus, in view of target gene silencing effects, it is preferable to use an siRNA molecule having a nucleotide bulge at positions 2-4 from the 5' end of the antisense molecule of the siRNA molecule or at positions 2-4 from the 3' end. It is more preferable to use an siRNA molecule having a single nucleotide bulge at position 2, 18 or 19.

Additionally, in order to compare thermodynamic stability between the siSurvivin and modified siSurvivins shown in FIG. 1 and a conventional 2'OMe-modified siRNA molecule found to have off-target effects, the following test was carried out. The siSurvivin-2'OMe is an siRNA molecule having a 2'OMe modification at the second nucleotide position of the antisense strand.

The melting temperatures (Tm) of the siSurvivin duplexes were measured using a Step-One real-time PCR machine (Applied Biosystems, Foster City, Calif.) and SYBR Green I Premix Ex Taq (TaKaRa, Bio Inc., Shiga, Japan) with SDS software version 2.0.1. The premix contained 1 μM of siSurvivin oligos. Sequences were denatured at 95° C. for 2 min and then subjected to a 10% ramp to 30° C. for a 10 min hold. Samples were then heated in 0.4° C. steps with 30 second holds to a final temperature of 95° C. The Tm values were computed from the melt curve analysis.

As a result, as can be seen in Table 1 below, the siRNAs having the single nucleotide bulge at positions 2 and 19 from the 5' end of the antisense strand were thermally stable. However, the siRNAs having the bulge at other positions showed a decrease in the Tm value, which is believed to influence gene silencing.

TABLE 1

| siRNA | Tm (° C.) | ΔTm (° C.) |
|---|---|---|
| siSurvivin | 59.61 | — |
| siSurvivin-2 | 61.45 | +1.84 |
| siSurvivin-3 | 55.94 | −3.67 |
| siSurvivin-4 | 56.44 | −3.17 |
| siSurvivin-5 | 56.28 | −3.33 |
| siSurvivin-16 | 56.28 | −3.33 |
| siSurvivin-17 | 55.27 | −4.34 |
| siSurvivin-18 | 55.44 | −4.17 |
| siSurvivin-19 | 58.2 | −1.41 |
| siSurvivin-2'OMe | 60.12 | +0.51 |

Example 2

Comparison of the Ability of siRNA Molecules having Single Nucleotide Bulge and Conventional siRNA Molecules to Discriminate Between Perfectly Matched and Mismatched Targets In order to examine the target sensitivity of the inventive siRNA molecules having the single nucleotide bulge and conventional siRNA molecules, the following test was carried out not only for the siRNA molecules having the single nucleotide bulge at positions 2, 18 and 19 (siSurvivin-2, siSurvivin-18, and siSurvivin-19), which were found to have excellent target gene silencing effects, but also for the conventional 19+2 siRNA molecule (siSurvivin).

Figure 3:
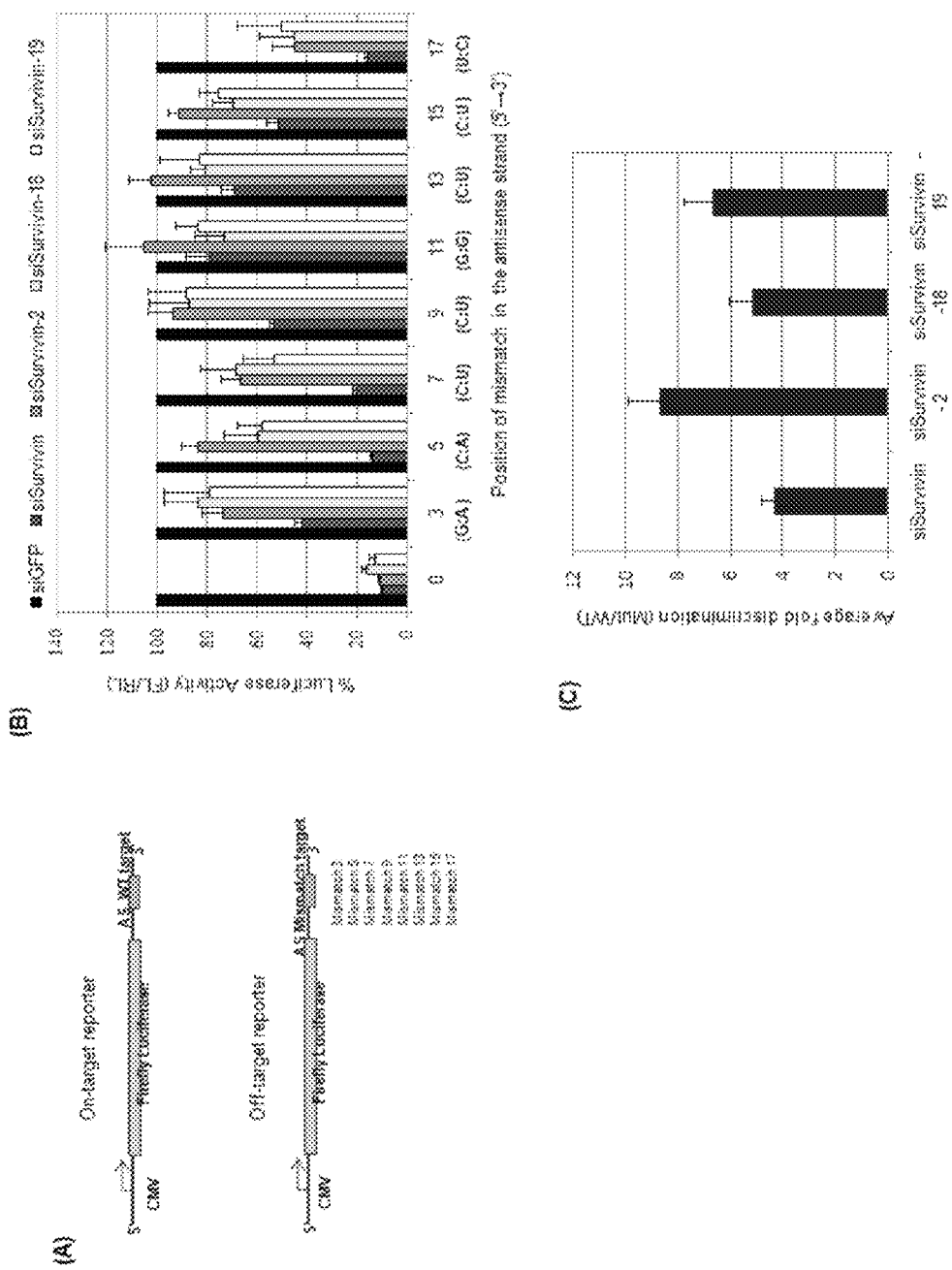
FIG. 3a is a schematic view showing a on-target or off-target luciferase reporter which is co-transfected into HeLa cells.
FIG. 3b is a graphic diagram showing luciferase activities measured to determine the off-target silencing effects of siSurvivin, siSurvivin-2, siSurvivin-18 and siSurvivin-19 for Survivin antisense targets (WT) and mismatched targets (siGFP: control)
FIG. 3c is a graphic diagram showing the average ratio of luciferase activity between the wild type and the mismatched targets.

First, pMIR clones containing wild type and mismatch types of siSurvivin antisense target sequences, respectively, were constructed in the same manner as Example 1 (FIG. 3a; the numbers in the names of mismatch targets indicate the positions of substitution).

```
                              (SEQ ID NO: 13)
Wild type:    5'-CTAGTAAGGAGATCAACATTTTCAA-3''
                              (SEQ ID NO: 14)
Mismatch 3:   5'-CTAGTAAGGAGATCAACATTTCCAA-3'
                              (SEQ ID NO: 15)
Mismatch 5:   5'-CTAGTAAGGAGATCAACATCTTCAA-3'
                              (SEQ ID NO: 16)
Mismatch 7:   5'-CTAGTAAGGAGATCAACCTTTTCAA-3'
                              (SEQ ID NO: 17)
Mismatch 9:   5'-CTAGTAAGGAGATCACCATTTTCAA-3'
                              (SEQ ID NO: 18)
Mismatch 11:  5'-CTAGTAAGGAGATGAACATTTTCAA-3'
                              (SEQ ID NO: 19)
Mismatch 13:  5'-CTAGTAAGGAGCTCAACATTTTCAA-3'
                              (SEQ ID NO: 20)
Mismatch 15:  5'-CTAGTAAGGCGATCAACATTTTCAA-3'
                              (SEQ ID NO: 21)
Mismatch 17:  5'-CTAGTAATGAGATCAACATTTTCAA-3'
```

Hela cells were transfected with vectors containing the wild type and mismatch targets, and then 10 nM of each of siSurvivin, siSurvivin-2, siSurvivin-18 and siSurvivin-19 was introduced into the cells. Then, luciferase activity in the cells was measured.

As a result, as can be seen in FIG. 3b, the effects of the siRNA molecules according to the present invention on the silencing of targets having no mismatch were reduced compared to the conventional siRNA, suggesting that the siRNA molecules according to the present invention reduces off-target effects caused by the antisense strand.

Additionally, in order to examine the ability to discriminate between a matched target sequence having no mismatch region and a mismatched target sequence having a substitution of one nucleotide, the ratio of luciferase activity between the wild type and the mismatched target was calculated. As a result, as can be seen in FIG. 3c, siSurvivin-2 was found to be an siRNA molecule which has the best target selectivity, because it had a low efficiency of silencing of the mismatched target and specifically silenced the complete target.

Example 3

Comparison of Off-Target Selectivity Between siRNA Molecules According to the Present Invention and 2'OMe-Modified siRNA Molecules In order to compare off-target selectivity between the inventive siRNA molecules having the single nucleotide bulge and a conventional 2'OMe-modified siRNA molecule found to have off-target effects, the following test was carried out.

First, as shown in FIG. 4, siSurvivin, siSurvivin-2 'A', siSurvivin-2 'C' and siSurvivin-2'OMe were prepared. In FIG. 4, siSurvivin-2 'A' indicates an siRNA molecule having A introduced at position 2 of the antisense strand; siSurvivin-2 'C' indicates an siRNA molecule having C introduced at position 2 of the antisense strand; siSurvivin-2'OMe indicates an siRNA molecule having a 2'OMe modification at position 2 of the antisense strand; the red color indicates a bulge nucleotide; and the blue color indicates a 2'OMe-modified nucleotide.

For the siRNA molecules shown in FIG. 4, a test for examining sensitivity to the targets was carried out in the same manner as Example 2. Additionally, in order to examine whether the siRNAs maintain on- vs off-target selection even at higher concentrations, the siRNAs were tested at concentrations of 10, 25 and 50 nM.

The $IC_{50}$ values of siRNA molecules of siSurvivin-2 'A', siSurvivin-2 'C' and siSurvivin-2'OMe for endogenous Survivin mRNA (on-target) were measured. As a result, as shown in FIG. 5, the inventive siRNA molecules having the single nucleotide bulge had $IC_{50}$ values similar to siSurvivin, whereas the 2'-OMe-modified siRNA had an $IC_{50}$ value higher than siSurvivin, suggesting that the gene silencing efficiency of the 2'-OMe-modified siRNA is slightly lost.

Figure 6:
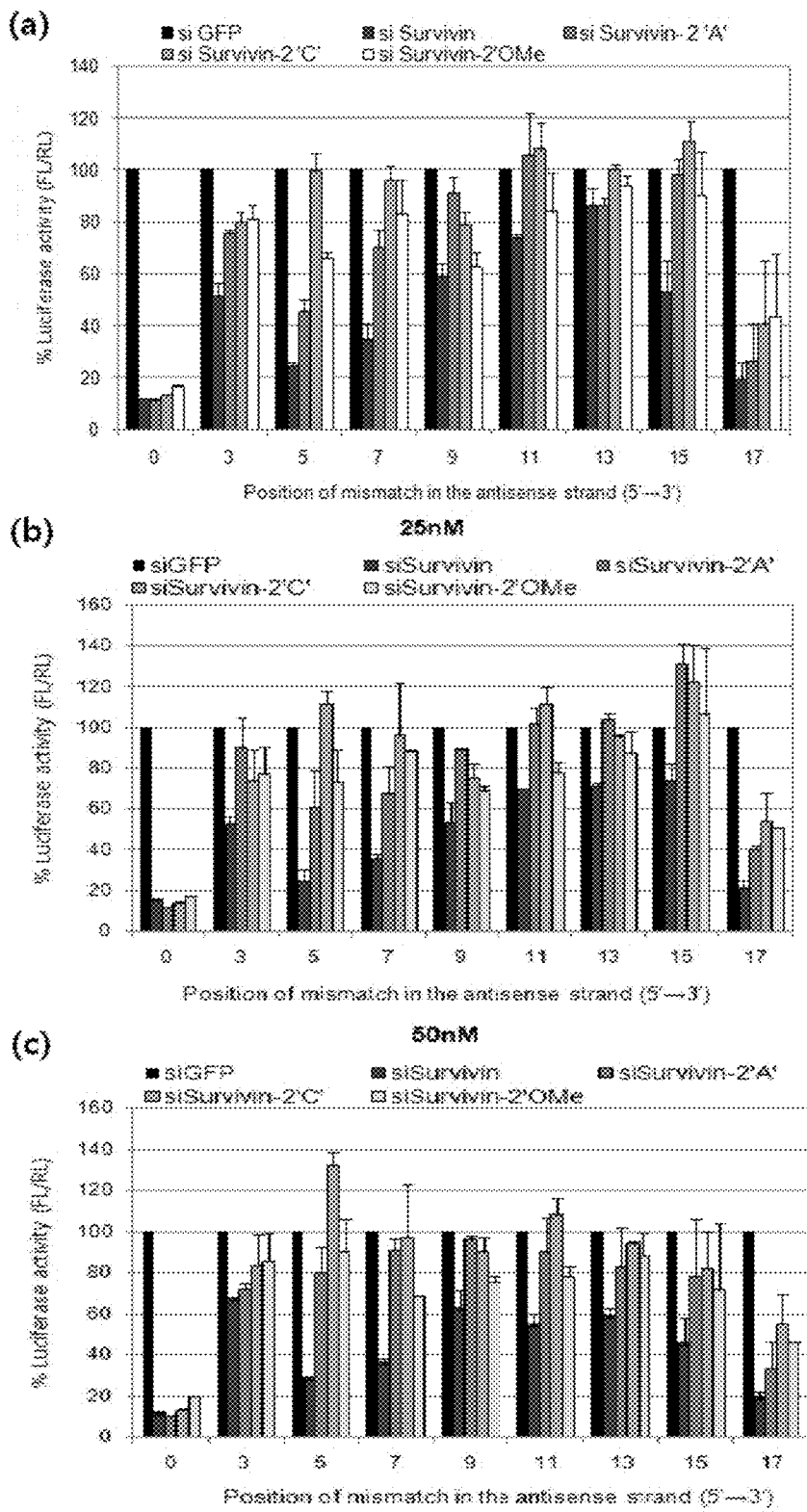
FIG. 6 is a set of graphs showing liciferase activities measured to determine the off-target silencing effects of siRNA of FIG. 4 for Survivin antisense targets (WT) and mismatched targets (siGFP: control). Specifically.

In addition, off-target silencing at each of concentrations of 10, 25 and 50 nM was measured. As a result, as can be seen in FIGS. 6 and 7, the siRNA molecule having the bulge at position 2 had the best target selectivity. Particularly, this siRNA molecule had significantly excellent target selectivity compared to the 2'OMe-modified siRNA molecule known to have off-target effects.

Example 4

Comparison (2) of Off-Target Selectivity between Inventive siRNA Molecule and 2'OMe-Modified siRNA Molecule In order to examine whether the test results of Examples 1 to 3 are specific only to an siRNA (siSurvivin) for Survivin or can also be applied to other siRNAs, the following additional test was performed.

First, in order to examine the possibility of application to an siRNA (siMPHOSPH1) for MPHOSPH1, siMPHOSPH1, siMPHOSPH1-2 'A', siMPHOSPH1-2 'G' and siMPHOS1-2'OMe were prepared as shown in FIG. 8. In FIG. 8, siMPHOS1-2 'A' indicates an siRNA molecule having A introduced at the second position of the antisense strand; siMPHOS1-2 'G' indicates an siRNA molecule having G introduced at the second position of the antisense strand; siMPHOSPH1-2'OMe indicates an siRNA having a 2'OMe modification at the second nucleotide position of the antisense strand; the red color indicates a bulge nucleotide; and the blue color indicates a 2'OMe-modified nucleotide.

For the siRNA shown in FIG. 8, a test for examining sensitivity to the targets was carried out in the same manner as Example 4. Herein, siMMPHOSPH1 antisense target oligo (wild type) and its mutants (mismatches), which are introduced into pMIR, are as follows:

```
                                              (SEQ ID NO: 29)
Wild type:    5'-CTAGTGACATGCGAATGACACTAGA-3'

(SEQ ID NO: 30)
Mismatch 5:   5'-CTAGTGACATGCGAATGACTCTAGA-3'

(SEQ ID NO: 31)
Mismatch 7:   5'-CTAGTGACATGCGAATGTCACTAGA-3'
```

The $IC_{50}$ values of siRNA molecules of siMPHOSPH1, siMPHOSPH1-2 'A', siMPHOSPH1-2 'G' and siMPHOSPH1-2'OMe for endogenous MPHOSPH1 mRNA (on-target) were measured. As a result, as can be seen in FIG. 9, unmodified siMPHOSPH1 showed an on-target silencing efficiency of only 45% at 10 nM, suggesting that it is inefficient. Also, the gene silencing efficiency of the 2'-OMe-modified siRNA was lower than that of the unmodified siMPHOSPH1. However, the inventive siRNA molecules having single nucleotide bulge showed an on-target silencing efficiency of up to 70% at 10 nM, suggesting that they have excellent silencing efficiency.

Figure 10:
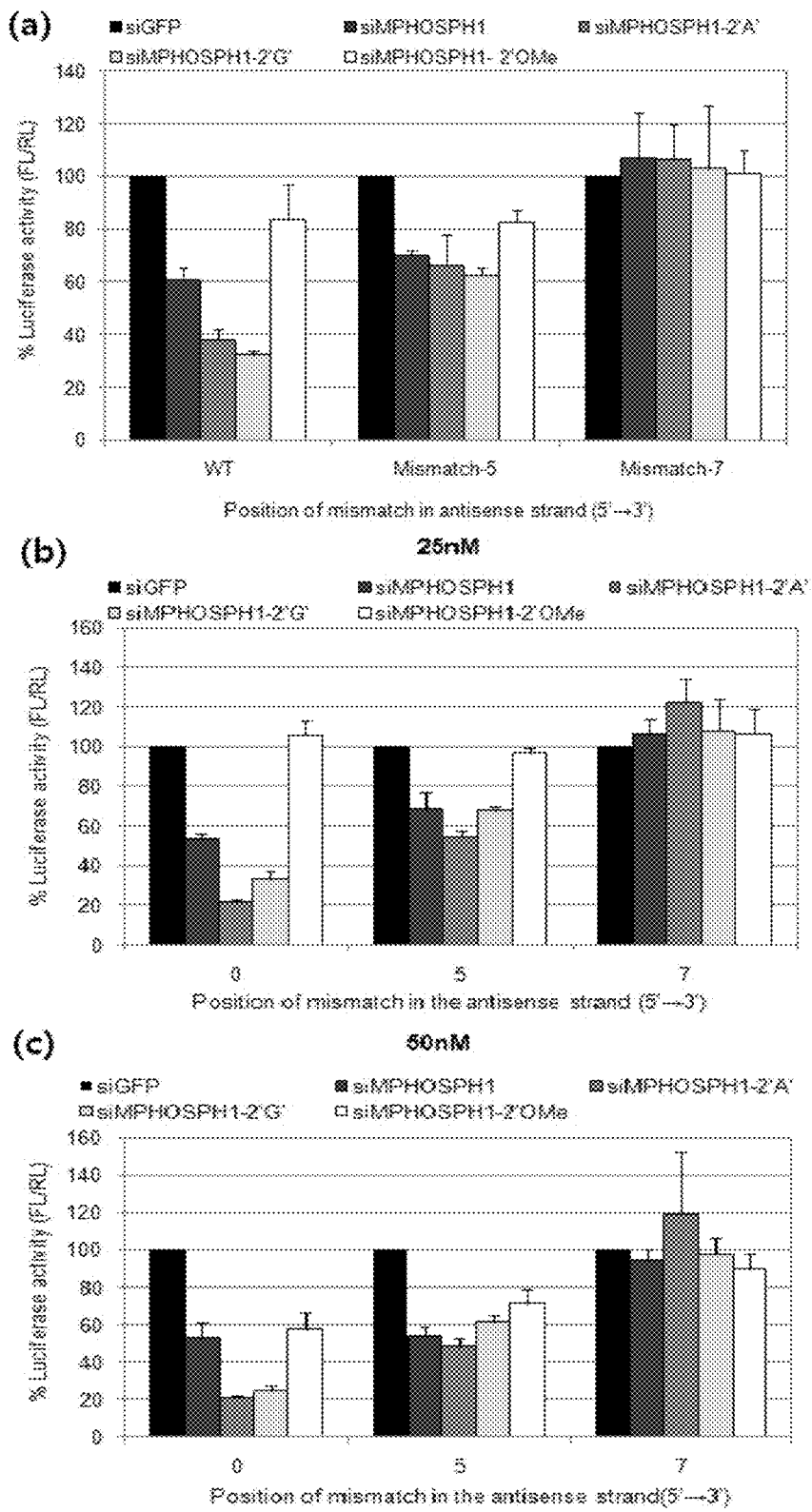
FIG. 10 is a set of graphs showing luciferase activities measured to determine the off-target silencing effects of siRNAs of FIG. 8 for a MPHOSPH1 antisense target (WT) and mismatched targets (siGFP: control). Specifically.

In addition, off-target silencing at a concentration of each of 10, 25 and 50 nM was measured. As a result, as can be seen in FIGS. 10 and 11, in the case of siMPHOSPH1, the siRNA molecules having the bulge at position 2 had excellent target selectivity, like the case of siSurvivin. Furthermore, these siRNA molecules showed significantly excellent target selectivity compared to the 2'OMe-modified siRNA molecule known to have off-target effects.

In addition, in order to examine the possibility of application to siRNA (siMAPK14) for MAPK14, siMAPK14, siMAPK14-2 'G', siMAPK14-2 'C' and siMAPK14-2'OMe were prepared as shown in FIG. 12. In FIG. 12, siMAPK14-2 'G' indicates an siRNA molecule having G introduced at position 2 of the antisense strand; siMAPK14-2 'C' indicates an siRNA molecule having C introduced at position 2 of the antisense strand; siMAPK14-2'OMe indicates an siRNA molecule having a 2'OMe modification at position 2 of the antisense strand; the red color indicates a bulge nucleotide, and the blue color indicates a 2'OMe-modified nucleotide.

For the siRNA molecules shown in FIG. 12, a test for examining sensitivity to the targets was carried out in the same manner as Example 3. Herein, siMAPK14 antisense target oligo (wild type) and its mutants (mismatches), which are introduced into pMIR, are as follows:

```
                                              (SEQ ID NO: 37)
Wild type:    5'-CTAGTCCTACAGAGAACTGCGGTTA-3'

(SEQ ID NO: 38)
Mismatch 5:   5'-CTAGTCCTACAGAGAACTGTGGTTA-3'

(SEQ ID NO: 39)
Mismatch 7:   5'-CTAGTCCTACAGAGAACAGCGGTTA-3'
```

Figure 13:
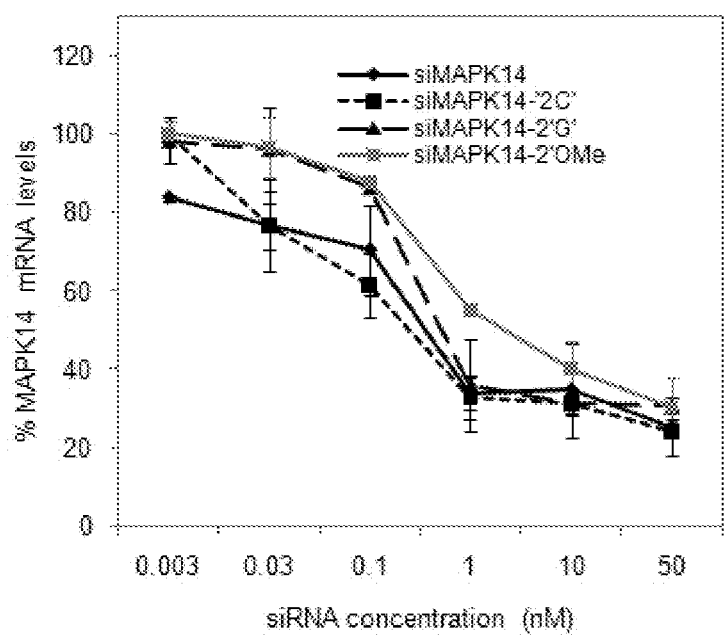
FIG. 13 is a graphic diagram showing the $IC_{50}$ values of siRNAs, which are siMAPK14, siMAPK14-2 'G', siMAPK14-2 'C' and siMAPK14-2'OMe, for endogenous MAPK14 mRNA.

The $IC_{50}$ values of siRNA molecules of siMAPK14, siMAPK14-2 'G', siMAPK14-2 'C' and siMAPK14-2'OMe for endogenous MAPK14 mRNA (on-target) were measured. As a result, as can be seen in FIG. 13, the 2'OMe-modified siMAPK14-2'OMe ($IC_{50}$ 1.79 nM) had a significantly high $IC_{50}$ value compared to the unmodified siMAPK14 ($IC_{50}$ 324 pM), suggesting that there is a loss in gene silencing efficiency. On the other hand, siMAPK14-2 'C' showed an $IC_{50}$ value similar to the unmodified siMAPK14. However, in the case of siMAPK14-2 'G', there was a loss in gene silencing efficiency, suggesting that the 'G' position which is the bulge nucleotide in this siRNA structure can form a wobble pair with the neighboring nucleotides of the sense strand.

Figure 15:
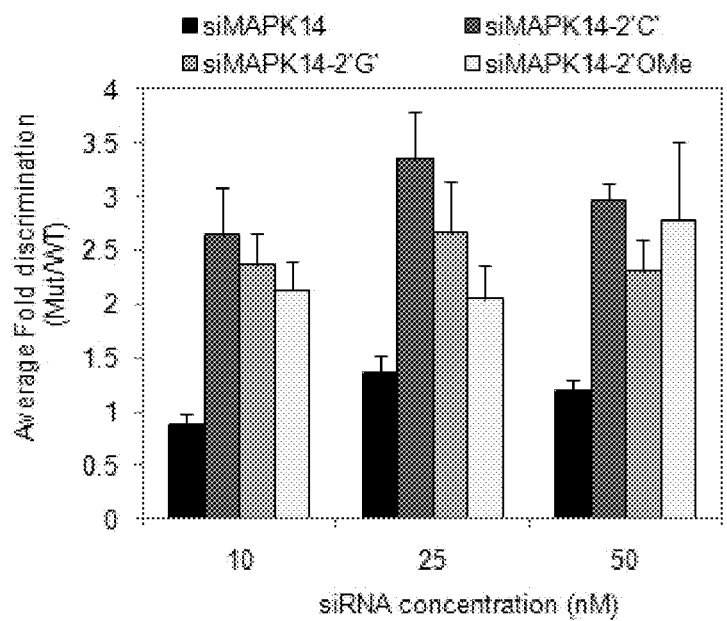
FIG. 15 is a graphic diagram showing the average ratio of luciferase activity between wild type and mismatched targets for the siRNAs of FIG. 12.

In addition, off-target silencing at a concentration of each of 10, 25 and 50 nM was measured. As a result, as can be seen in FIGS. 14 and 15, in the case of siMAPK14, the siRNA molecules having the bulge at position 2 had the best target selectivity, like the case of siSurvivin or siMPHOS1. In addition, it could be concluded that these siRNA molecules show significantly excellent target selectivity compared to the 2'OMe-modified siRNA molecule known to have off-target effects.

Putting such test results together, it can be seen that the siRNA structure according to the present invention is not applied only to specific siRNAs and that any siRNA having the same structure reduces off-target effects mediated by the antisense strand and has an improved ability to select a target.

Example 5

Measurement of the Ability of Asymmetric 16+3A siRNA Structure Having Single Nucleotide Bulge to Reduce Off-Target Effects In order to confirm whether off-target effects are reduced when the siRNA structure of the present invention is applied to the 16+3A siRNA structure previously found by the present inventors to minimize off-target effects caused by the sense strand, the following test was carried out for siSurvivin-2 'C', siSurvivin having a 16+3A structure (siSurvivin 16+3A), and 16+3A siSurvivin having a single nucleotide bulge at position 2 of the antisense strand (siSurvivin16+3A-2'C').

The 16+3A structure refers to a structure comprising a 19-nt antisense strand and a 16-nt sense strand and having an overhang at the 3' end of the antisense strand, among siRNA molecules comprising a 19-21-nucleotide (nt) antisense strand and a 15-19-nt sense strand having a sequence complementary to the antisense strand, wherein the 5' end of the antisense strand is a blunt end, and the 3' end of the antisense strand has an overhang. In addition, siSurvivin 16+3A and siSurvivin16+3A-2'C' are as follows:

```
siSurvivin 16 + 3A
                                      (SEQ ID NO: 40)
Antisense:      5'-UGAAAAUGUUGAUCUCCUU-3'

(SEQ ID NO: 41)
Sense:          5'-GAGAUCAACAUUUUCA-3' siSurvivin16 + 3A-2'C'
                                      (SEQ ID NO: 42)
Antisense:      5'-UCGAAAAUGUUGAUCUCCUU-3'

(SEQ ID NO: 41)
Sense:          5'-GAGAUCAACAUUUUCA-3'
```

Figure 16:
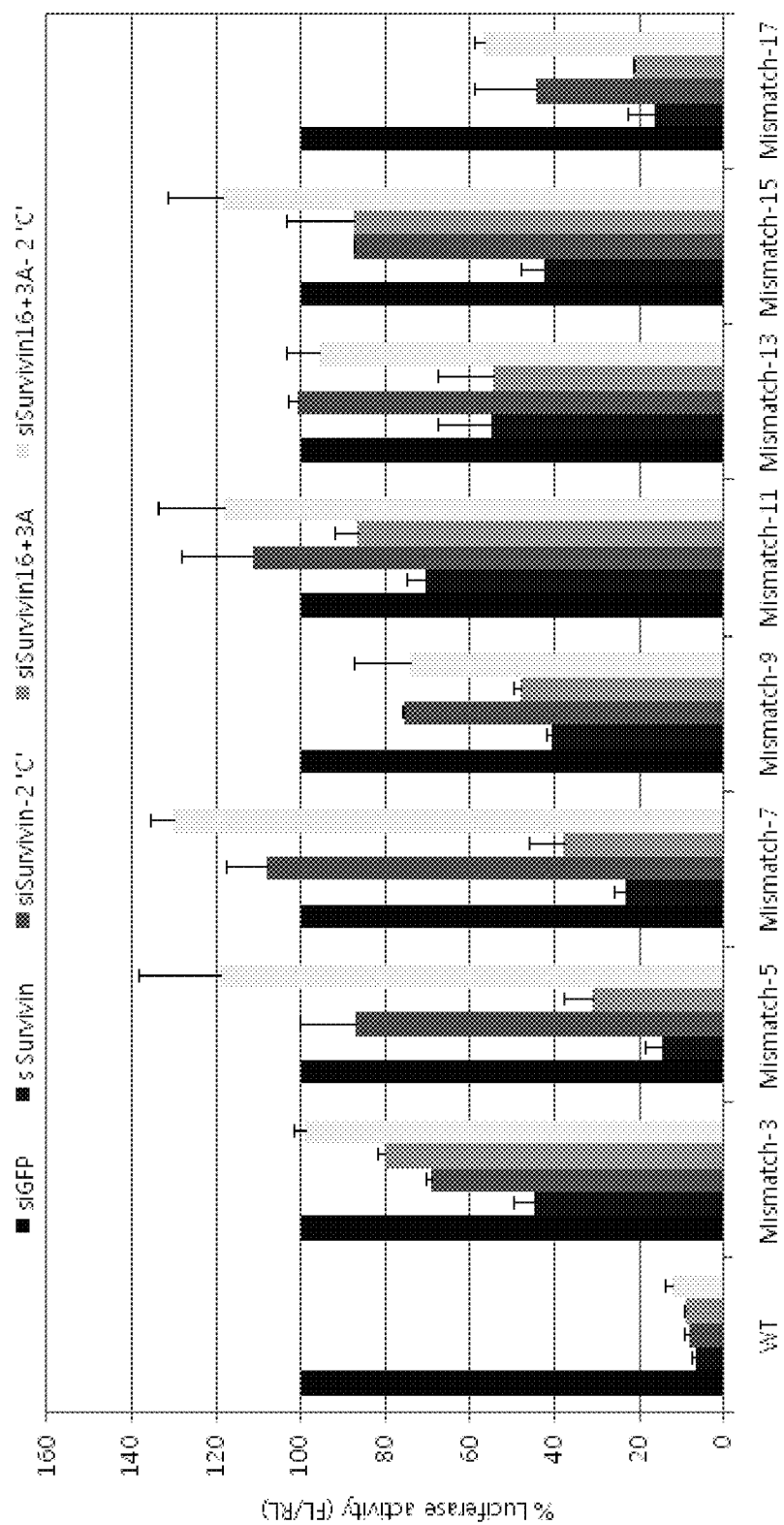
FIG. 16 is a graphic diagram showing luciferase activities measured to determine the off-target silencing effects of siRNAs, which are siSurvivin, siSurvivin-2 'C', siSurvivin 16+3A and siSurvivin16+3A-2'C', for Survivin antisense targets (WT) and mismatched targets (siGFP: control).
Figure 17:
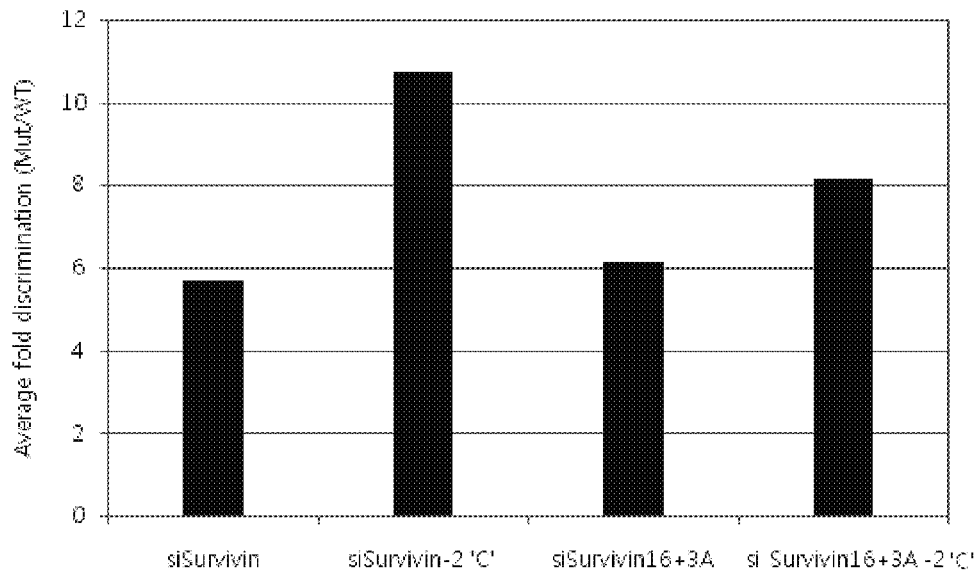
FIG. 17 is a graphic diagram showing the average ratio of luciferase activity between wild type and mismatched targets for siSurvivin, siSurvivin-2 'C', siSurvivin 16+3A and siSurvivin16+3A-2'C'.

For the above siRNAs, luciferase activity was measured in the same manner as Example 2. As a result, as can be seen in FIGS. 16 and 17, when a single nucleotide bulge was introduced into the antisense strand of the 16+3A siRNA, off-target effects caused by the antisense strand were effectively reduced.

Meanwhile, in order to examine whether the siRNA molecules have the effect of reducing off-target effects mediated by the sense strand, a test for examining the gene silencing effects of the siRNA molecules was performed in the same manner as Example 2 using the sense strand as a target. Herein, an siSurvivin sense target oligo introduced into pMIR is as follows:

```
siSurvivin sense target oligo
                                      (SEQ ID NO: 43)
5'-CTAGTTGAAAATGTTGATCTCCTTA-3'
```

Figure 18:
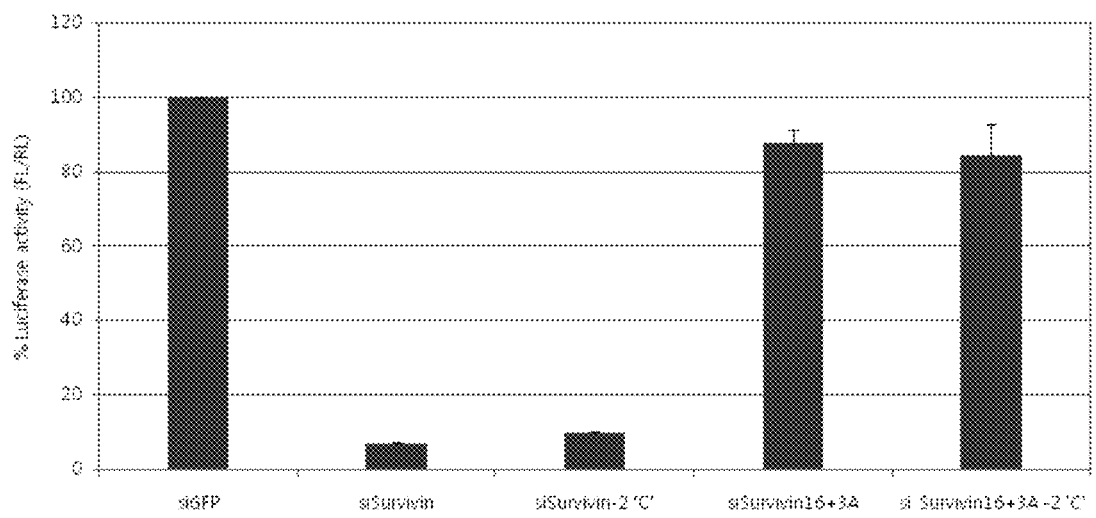
FIG. 18 is a graphic diagram showing luciferase activities measured to determine the off-target effects of siSurvivin, siSurvivin-2 'C', siSurvivin 16+3A and siSurvivin16+3A-2'C' for sense Survivin targets.

As a result, as can be seen in FIG. 18, the ability of the inventive siRNA molecule to reduce off-target effects mediated by the antisense strand slightly increased compared to that of the conventional siRNA molecule, but was a low level. However, in the case of siSurvivin16+3A-2'C' obtained by applying the structure of the present invention to the conventional 16+3A structure, the ability to reduce off-target effects mediated by the sense strand was almost similar to that of the conventional 16+3A siRNA molecule (siSurvivin16+3A).

Accordingly, it could be seen that, when the asymmetric structure was applied to the siRNA molecule of the present invention, an excellent siRNA molecule that minimizes all off-target effects mediated by the sense and antisense strands could be obtained.

Example 6

Comparison of siRNA Molecules of the Present Invention with Mismatched siRNAs (Fork-siRNAs)

It is known that the so-called "fork-siRNAs" having a single nucleotide mismatch at the 3' end of the sense strand promote the introduction of the antisense strand into RISC and reduce sense strand-mediated RNAi. Thus, in order to examine whether the bulge structure of the present invention generates a structure similar to "fork-siRNA", the following test was carried out.

First, as shown in FIG. 19, siRNA and fork-siRNAs were prepared. Then, a test for examining sensitivity to the targets was carried out in the same manner as Examples 2 and 4.

As a result, as can be seen in FIG. 20, the fork-siRNA did not show a decrease in off-target silencing for all the three mRNAs. Furthermore, as can be seen in FIG. 20c, the gene silencing efficiency of siMPHOSPH1-fork was not improved compared to that of siMPHOSPH1.

Such results indicate that the siRNA molecule of the present invention structurally and functionally differs from the fork modifications.

Example 7

Examination of siRNA-Mediated Toxicity of the siRNA Molecule According to the Present Invention Antisense strand-driven silencing of undesired, imperfectly matched mRNAs is a siRNA-mediated side effect. Some siRNAs have been shown to inhibit cell viability without significantly silencing on-targeting transcripts, indicating that these are false positive phenotypes. Thus, siRNA modifications for reducing antisense off-target silencing should reduce such phenotypes. Accordingly, the effects of the mutants on an siRNA-mediated loss in cell viability were assessed using an MTT assay.

Cell viability was measured using an MTT colorimetric assay (TaKaRA, Bio Inc., Shiga, Japan) according to the manufacturer's protocol. Shortly, HeLa cells seeded on a 96-well plate were transfected with 10 nM of siRNA, and after 96 hours, 20 μl of MTT reagent was added to 100 μl of complete medium. Then, the cells were incubated in a humidified atmosphere with 5% $CO_2$ at 37° C. for 30 minutes.

The growth medium was removed and 100 μl of complete DMSO (dimethyl sulphoxide) was added to each well. The plate was kept in a shaker for 5 minutes, and then the change in color was measured with an ELISA plate reader at 540 nm using 620 nm as a reference wavelength. All absorbance values were corrected against a blank that contained medium alone. Percent cell viability was calculated considering the untreated control as 100% viable. The $IC_{50}$ value was calculated using Sigma plot 10.0.

Figure 21:
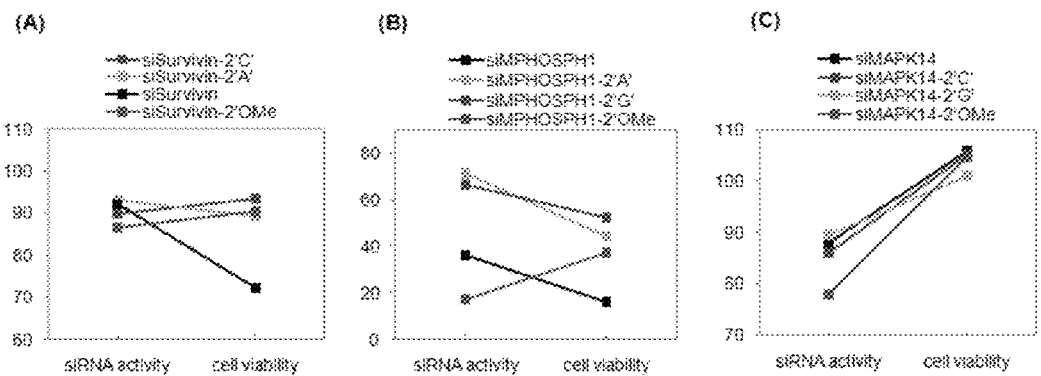
FIG. 21 is a set of graphs showing the results of measurement of siRNA activity and HeLa cell viability for each of siRNAs.

As a result, as shown in FIG. 21, no cell death was observed in the case of siMAPK-14, whereas a significant decrease in cell viability was observed in the HeLa cells transfected with 10 nM of siSurvivin and siMPHOSPH-1. In comparison with Lipofectamine 2000-treated cells (control) considered 100% viable, the cells transfected with the unmodified siSurvivin showed a cell viability of 72%. On the other hand, in the case of the bulge modifications according to the present invention, cell viability increased to about 92% with no loss in silencing activity. Meanwhile, the siSurvivin 2'-OMe modification was also shown to reduce siRNA-mediated cell death.

Unlike siSurvivin, siMPHOSPH-1 was found to have very strong toxicity. siMPHOSPH-1 resulted in a high level of cell death (85%), which was independent of the antisense silencing activity. On the other hand, the bulge modification was shown to increase silencing activity and also to reduce the cell death considerably (FIG. 21b).

Example 8

Examination (1) of Reduction in Off-Target Effects in Genome Wide Microarray

In order to re-confirm the finding obtained by the luciferase reporter analysis of Examples 1 to 5, a microarray was performed for cDNA prepared from Hela cells treated with each of unmodified siSurvivin and the siSurvivin structure of the present invention.

Specifically, total RNAs were extracted using TRI Reagent® (Ambion) and RNeasy® mini kit (Qiagen) according to the manufacturer's protocol. 10 μg of each of the total RNAs was synthesized into double-stranded cDNA (dscDNA) using an Invitrogen's kit. The samples were precipitated with ethanol. 1 μg of the dscDNA was used for labeling by Klenow fragment (NEB) using Cy3-labelled 9mer (TriLink Biotechnologies), and labeled samples were precipitated using isopropanol. 4 μg of Cy3-labeled DNA (containing sample tracking control and alignment oligo) was hybridized to Nimblegen 385K 4-plex human microarray at 42° C. for 18 hours using the Nimblegen Hybridization system (Nimblegen). Arrays were washed and array images were obtained using a GenePix 4000B scanner (Axon Instruments). Scanned images were imported into NimbleScan software (Nimblegen). Expression data were normalized through quantile normalization (quantile normalization; Biopharm Stat. 2004 August; 14(3):575-89. Effect of normalization on significance testing for oligonucleotide microarrays. Parrish R S, Spencer H J 3rd) and Robust Multichip Average (RMA) algorithm (Effects of filtering by Present call on analysis of microarray experiments. McClintick J N, Edenberg H J. BMC Bioinformatics. 2006 Jan. 31; 7:49).

The changes in the expressions of 24,000 genes for siSurvivin structures relative to the siGFP control were calculated, and genes showing a 2-fold or more decrease in the expression level due to the siSurvivin structures were selected. Matching of the 3' UTR of the selected genes with 2-8 seed nucleotides was performed using BLAST. Two times or more silenced transcripts having matches of the 3' UTR of mRNA with 2-8 seed nucleotides were considered as antisense off-targets.

Figure 22:
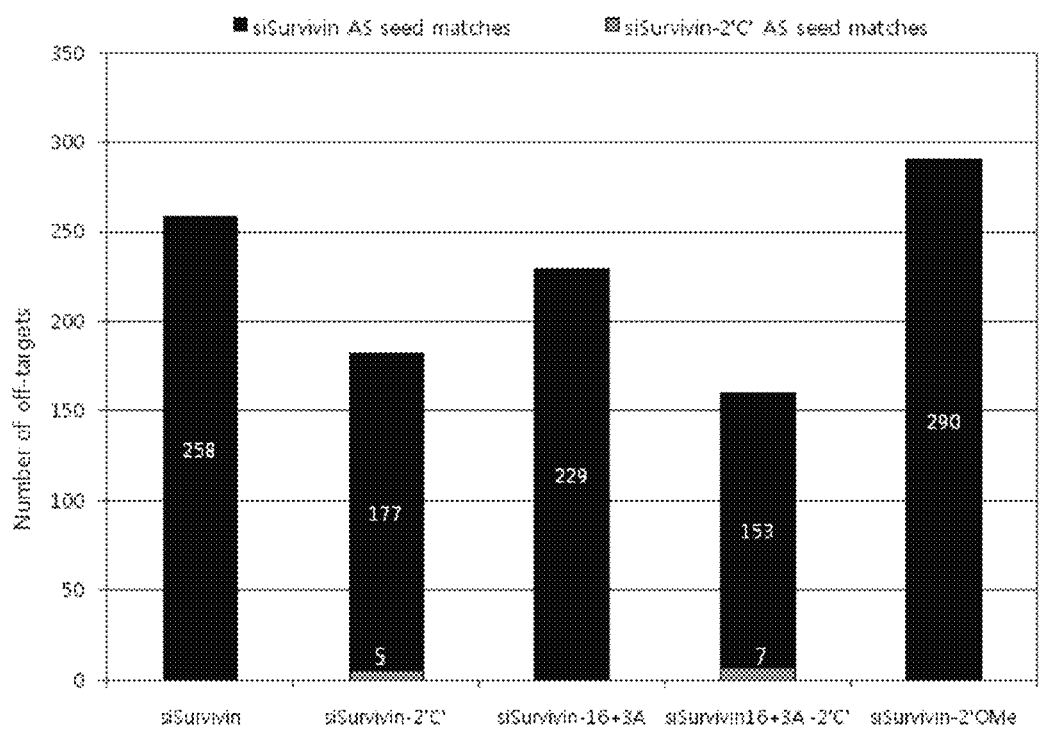
FIG. 22 is a graphic diagram showing the number of off-target genes, measured in the genome wide microarray of each of siSurvivin, siSurvivin-2 'C', siSurvivin 16+3A, siSurvivin16+3A-2'C' and siSurvivin-2'OMe.

As a result, as shown in FIG. 22, the siRNA molecules of the present invention, such as siSurvivin-2 'C' and siSurvivin16+3A-2 'C', showed a considerably small number of off-target genes. Particularly, the siSurvivin-2'OMe modified with 2'OME known to reduce off-target effects showed a larger number of off-target genes than the unmodified siSurvivin. In other words, the effect of reducing off-targets could not be observed in the 2'OMe-modified siRNA.

Examples 9

Examination (2) of Reduction in Off-Target Effects in Genome Wide Microarray

In order to analyze the effect of the siRNA structure of the present invention on off-target silencing in cells and re-confirm the finding obtained by the above luciferase reporter analysis, genome wide expression profiling was performed using cDNA prepared from HeLa cells treated with each of modified siSurvivin and unmodified siSurvivin.

Total RNA was extracted in the same manner as Example 8. 4 μg of Cy3-labeled DNA (containing sample tracking control and alignment oligo) was hybridized to Nimblegen 385K 4-plex human microarray at 42° C. for 18 hours using Nimblegen hybridization system (Nimblegen). Then, arrays were washed and array images were obtained using InnoScan® 900 scanner (Innopsys, Carbonne, France). Scanned images were imported into Mapix software (Innopysys). Expression data were normalized through quantile normalization (quantile normalization; Biopharm Stat. 2004 August; 14(3):575-89. Effect of normalization on significance testing for oligonucleotide microarrays. Parrish R S, Spencer H J 3rd) and Robust Multichip Average (RMA) algorithm (Effects of filtering by Present call on analysis of microarray experiments. McClintick J N, Edenberg H J. BMC Bioinformatics. 2006 Jan. 31; 7:49).

In this test, 0.3% of transcripts were removed from either end of the intensity distribution as outliers, leaving 23856 to be used in this test. Of these, 18978 sequences that represented the RefSeq human mRNA sequences were used for analysis. siSurvivin antisense and sense seeds (nucleotides 2-8, 2-7, 1-7) were matched with all distinct human RefSeq 3'-UTRs using Target Rank. Overall changes in the mRNA level of transcriptions with or without siRNA seed matches were visualized with MA plots.

First, the homology of mRNA with the seed region of the guide strand (positions 1-8, 2-8 and 1-7 from the 5' end) was determined, and transcripts having a 3'-UTR showing homology with the antisense seed region were determined to be 10.7% (n=2031) of the whole transcripts. Because transcripts down-regulated by 50% or more are generally considered to have a significant effect on intracellular changes, transcripts silenced by 50% or more were considered as antisense off-targets.

In addition, transcripts having a 3'-UTR showing homology with the siSurvivin sense seed region were determined to be 2.7% (n=521) of the whole transcripts. Of these, transcripts silenced by 50% or more were considered as sense off-targets.

Moreover, because new off-target transcripts for a new seed region resulting from the modification or introduction of bases in the siRNA seed region can occur, homology to the modified antisense seeds was analyzed. Homology to the siSurvivin-2'C seed was analyzed, and as a result, transcripts having a 3'-UTR showing homology to the seed region were determined to be 0.5% (n=95) of the whole transcripts.

Figure 23:
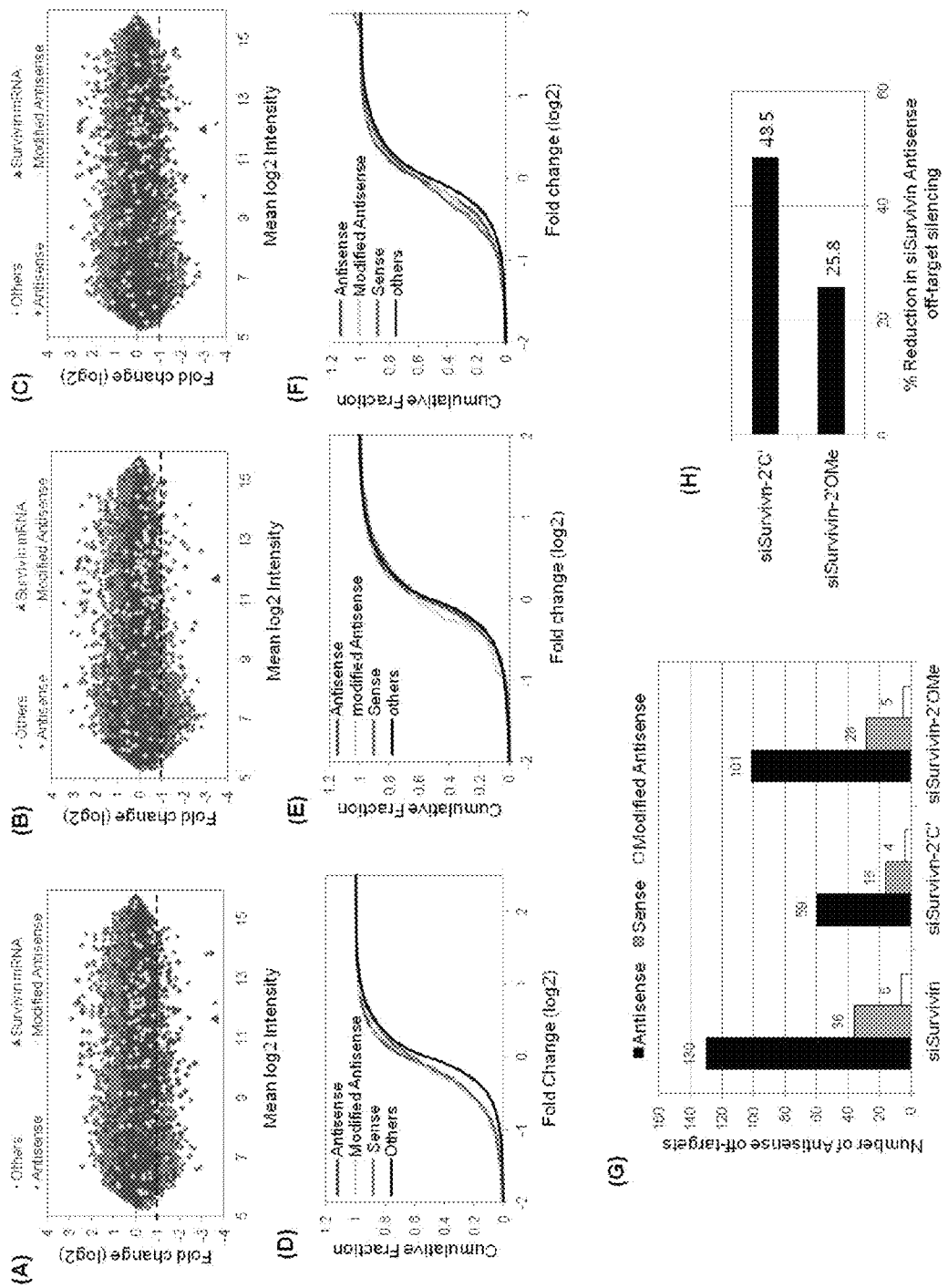
FIG. 23 shows the results obtained by performing the microarray-based genome wide off-target profiling of siSurvivin, siSurvivin-2'C' and siSurvivin-2OMe. Specifically.

As a result, as shown in FIG. 23, siSurvivin-2'C which is the siRNA molecule of the present invention showed a significantly small number of antisense off-targets compared to unmodified siSurvivin (n=130) and siSurivivin-2'OMe (n=101) (FIG. 23G). In addition, as can be seen in FIG. 23H, the degree of antisense off-target silencing was reduced up to 50%. However, this reduction could not be seen in the case of siSurvivin-2'OMe.

INDUSTRIAL APPLICABILITY

As described above, the siRNA molecule of the invention shows high target gene silencing efficiency while minimizing off-target effects caused by the antisense strand, and thus has improved target selectivity. Accordingly, the siRNA molecule of the invention can be substituted for conventional siRNA molecules and can be widely be used in siRNA-based gene silencing techniques, including gene therapy.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A double-stranded siRNA molecule comprising an antisense strand and a sense strand complementary to the antisense strand, wherein the siRNA molecule has at least one single nucleotide bulge having a gap without base-pairing formed by introducing a single nucleotide into the antisense strand, wherein the single nucleotide bulge is present at a second, eighteenth or nineteenth position from the 5' end region of antisense strand.

2. The double-stranded siRNA molecule of claim 1, wherein the single nucleotide bulge is present at a second position from the 5' end region of the antisense strand of the siRNA.

3. The double-stranded siRNA molecule of claim 1, wherein the introduced nucleotide is a nucleotide having a base different from that of a nucleotide which is adjacent thereto or an abasic nucleotide.

4. The double-stranded siRNA molecule of claim 1, wherein the siRNA molecule comprises a 19-21-nucleotide (nt) antisense strand and a 13-17-nt sense strand having a sequence complementary to the antisense strand, wherein the 5' end of the antisense strand is a blunt end, and the 3' end of the antisense strand has an overhang.

5. The double-stranded siRNA molecule of claim 4, wherein the length of the sense strand in the siRNA molecule is 15-16 nt, and the length of the overhang is 3-6 nt.

6. The double-stranded siRNA molecule of claim 1, wherein the siRNA molecule comprises a chemical modification.

7. The double-stranded siRNA molecule of claim 6, wherein the chemical modification is the substitution of the hydroxyl group at position 2' of the ribose of at least one nucleotide included in the siRNA by any one of a hydrogen atom, a fluorine atom, an -O-alkyl group, an -O-acyl group and an amino group.

8. The double-stranded siRNA molecule of claim 6, wherein the chemical modification is the substitution of the phosphate backbone of at least one nucleotide included in the siRNA by any one of a phosphorothioate form, a phosphorodithioate form, an alkylphosphonate form, a phosphoroamidate form and a boranophosphate form.

9. The double-stranded siRNA molecule of claim 6, wherein the chemical modification is the substitution of at least one nucleotide included in the siRNA by any one of LNA (locked nucleic acid), UNA (unlocked nucleic acid), morpholino, and PNA (peptide nucleic acid).

10. A gene silencing composition containing the siRNA molecule of claim 1.

11. A gene silencing kit containing the siRNA molecule of claim 1.

12. A method for silencing a target gene in a cell, the method comprising a step of introducing the siRNA molecule of claim 1 into the cell.

13. A method for silencing a target gene in a cell, the method comprising a step of expressing the siRNA molecule of claim 1 into the cell.

14. A method for suppressing off-target effects caused by the antisense strand of siRNA molecules, the method comprising a step of introducing the siRNA molecule of claim 1 into a cell.

15. A method for suppressing off-target effects caused by the antisense strand of siRNA molecules, the method comprising a step of expressing the siRNA molecule of claim 1 into a cell.

* * * * *